United States Patent
Bogen et al.

(10) Patent No.: US 10,899,788 B2
(45) Date of Patent: Jan. 26, 2021

(54) CYCLIC PHOSPHATE SUBSTITUTED NUCLEOSIDE COMPOUNDS AND METHODS OF USE THEREOF FOR THE TREATMENT OF VIRAL DISEASES

(71) Applicants: Stephane Bogen, Somerset, NJ (US); David Dukhan, Montpellier (FR); Guillaume Brandt, Grabels (FR); Claire Pierra Rouviere, Montarnaud (FR); Cyril B. Dousson, Canet (FR); Francois-Rene Alexandre, Montpellier (FR); MERCK SHARP & DOHME CORP., Rahway, NJ (US); IDENIX PHARMACEUTICALS LLC, Campbridge, MA (US)

(72) Inventors: Stephane Bogen, Somerset, NJ (US); David Dukhan, Montpellier (FR); Guillaume Brandt, Grabels (FR); Claire Pierra Rouviere, Montarnaud (FR); Cyril B. Dousson, Canet (FR); Francois-Rene Alexandre, Montpellier (FR)

(73) Assignees: Merck Sharp & Dohme Corp., Rahway, NJ (US); Idenix Pharmaceuticals LLC, Cambridge, MA (US)

( * ) Notice: Subject to any disclaimer, the term of this patent is extended or adjusted under 35 U.S.C. 154(b) by 0 days.

(21) Appl. No.: 16/311,363

(22) PCT Filed: Jun. 20, 2017

(86) PCT No.: PCT/US2017/038212
§ 371 (c)(1),
(2) Date: Dec. 19, 2018

(87) PCT Pub. No.: WO2017/223012
PCT Pub. Date: Dec. 28, 2017

(65) Prior Publication Data
US 2019/0233463 A1 Aug. 1, 2019

Related U.S. Application Data

(60) Provisional application No. 62/352,093, filed on Jun. 20, 2016.

(51) Int. Cl.
| | | |
|---|---|---|
| C07H 19/11 | (2006.01) |
| A61P 31/14 | (2006.01) |
| C07H 19/213 | (2006.01) |
| A61K 45/06 | (2006.01) |
| A61K 31/7072 | (2006.01) |
| A61K 31/7076 | (2006.01) |

(52) U.S. Cl.
CPC ....... *C07H 19/213* (2013.01); *A61K 31/7072* (2013.01); *A61K 31/7076* (2013.01); *A61K 45/06* (2013.01); *A61P 31/14* (2018.01); *C07H 19/11* (2013.01)

(58) Field of Classification Search
None
See application file for complete search history.

(56) References Cited

U.S. PATENT DOCUMENTS

| | | | |
|---|---|---|---|
| 7,879,815 B2 | 2/2011 | MacCoss et al. | |
| 9,296,778 B2* | 3/2016 | Parsy | A61K 31/7068 |
| 2013/0315867 A1* | 11/2013 | Parsy | A61K 45/06 424/85.7 |
| 2014/0161770 A1 | 6/2014 | Girijavallabhan et al. | |

FOREIGN PATENT DOCUMENTS

| | | |
|---|---|---|
| WO | 2010075517 | 7/2010 |
| WO | 2013177195 A1 | 11/2013 |
| WO | 2014058801 A1 | 4/2014 |

OTHER PUBLICATIONS

International Search Report and Written Opinion for PCT/US2017/038212, dated Sep. 5, 2017; 8 pages.

* cited by examiner

*Primary Examiner* — Traviss C McIntosh, III
(74) *Attorney, Agent, or Firm* — Jeffrey P. Bergman; Catherine D. Fitch

(57) ABSTRACT

The present invention relates to Cyclic Phosphate Substituted Nucleoside Compounds of Formula (I), and pharmaceutically acceptable salts thereof, wherein in A, B, $R^1$, $R^2$, $R^3$, Q and V are as defined herein. The present invention also relates to compositions comprising a Cyclic Phosphate Substituted Nucleoside Compound, and methods of using the Cyclic Phosphate Substituted Nucleoside Compounds for treating or preventing HCV infection in a patient.

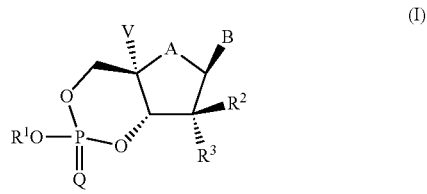

(I)

17 Claims, No Drawings

CYCLIC PHOSPHATE SUBSTITUTED NUCLEOSIDE COMPOUNDS AND METHODS OF USE THEREOF FOR THE TREATMENT OF VIRAL DISEASES

CROSS-REFERENCE TO RELATED APPLICATIONS

This application is the national stage application under 35 U.S.C. 371 of International Patent Application No. PCT/US17/038212, filed Jun. 20, 2017, which claims priority to U.S. Provisional Patent Application No. 62/352,093, filed Jun. 20, 2016. Each of the aforementioned applications is incorporated by reference in its entirety.

FIELD OF THE INVENTION

The present invention relates to Cyclic Phosphate Substituted Nucleoside Compounds, compositions comprising a Cyclic Phosphate Substituted Nucleoside Compound, and methods of using the Cyclic Phosphate Substituted Nucleoside Compounds for treating or preventing HCV infection in a patient.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. Once infected, about 20% of people clear the virus, but the rest harbor HCV the rest of their lives. Ten to twenty percent of chronically infected individuals eventually develop liver-destroying cirrhosis or cancer. HCV is transmitted parenterally by contaminated blood and blood products, contaminated needles, or sexually and vertically from infected mothers or carrier mothers to their off-spring.

Different approaches to HCV therapy have been taken, which include the inhibition of viral serine proteinase (NS3 protease), helicase, and RNA-dependent RNA polymerase (NS5B), and the development of a vaccine. Current and investigational treatments for HCV infection are reviewed in Poordad et al., Treating hepatitis C: current standard of care. Emerging direct-acting antiviral agents are discussed in Poordad et al., *Journal of Viral Hepatitis* 19: 449-464 (2012); and Asselah et al., Protease and polymerase inhibitors for the treatment of hepatitis C, *Liver International* 29(s1): 57-67 (2009). The changing therapeutic landscape for hepatitis C is discussed in Dore, *Med. J. Australia* 196: 629-632 (2012); and Balsano, *Mini Rev. Med. Chem.* 8(4): 307-318 (2008). Despite the availability of therapeutic treatment options, chronic HCV infection remains a major healthcare concern. Moreover, there is no established vaccine for HCV. Consequently, there is a need for improved therapeutic agents that effectively combat chronic HCV infection.

The HCV virion is an enveloped positive-strand RNA virus with a single oligoribonucleotide genomic sequence of about 9400 bases which encodes a polyprotein of about 3,000 amino acids. The protein products of the HCV gene consist of the structural proteins C, E1, and E2, and the non-structural proteins NS2, NS3, NS4A, NS4B, NS5A and NS5B. The nonstructural (NS) proteins are believed to provide the catalytic machinery for viral replication.

The NS3 protease releases NS5B, the RNA-dependent RNA polymerase from the polyprotein chain. HCV NS5B polymerase is required for the synthesis of a negative-strand RNA intermediate compound from a positive-strand genomic viral RNA that serves as a template in the replication cycle of HCV. NS5B polymerase is an essential component in the HCV replication complex. See K. Ishi, et al., "Expression of Hepatitis C Virus NS5B Protein: Characterization of Its RNA Polymerase Activity and RNA Binding," *Hepatology*, 29:1227-1235 (1999) and V. Lohmann, et al., "Biochemical and Kinetic Analyses of NS5B RNA-Dependent RNA Polymerase of the Hepatitis C Virus," *Virology*, 249: 108-118 (1998). Inhibition of HCV NS5B polymerase prevents formation of the double-stranded HCV RNA and therefore constitutes an attractive approach to the development of HCV-specific antiviral therapies.

The development of inhibitors of HCV NS5B polymerase with potential for the treatment of HCV infection has been reviewed in Poordad et al. (2012), supra; Asselah et al. (2009), supra; and Chatel-Chaix et al. Direct-acting and host-targeting HCV inhibitors: current and future directions. *Current Opinion in Virology*, 2:588-598 (2012). The activity of purine ribonucleosides against HCV polymerase was reported by A. E. Eldrup et al., "Structure-Activity Relationship of Purine Ribonucleosides for Inhibition of HCV RNA-Dependent RNA Polymerase," *J. Med. Chem.*, 47:2283-2295 (2004).

SUMMARY OF THE INVENTION

In one aspect, the present invention provides Compounds of Formula (I):

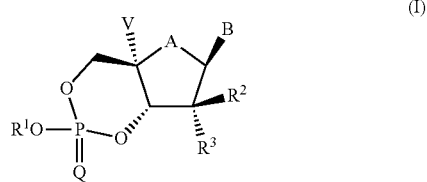

or a pharmaceutically acceptable salt thereof,
wherein:
A is selected from O, S and $CH_2$;
B is selected from one of the following groups:

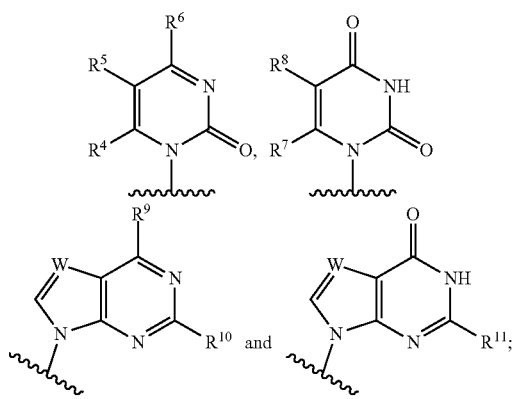

Q is O or S;
V is H, halo or $-N(R^{12})_2$;
W is N, CH or CF;
$R^1$ is $-(CH_2)_m-C(O)OR^{13}$;

$R^2$ is selected from H, F, Cl, $C_1$-$C_3$ alkyl and $C_2$-$C_3$ alkynyl;

$R^3$ is selected from $C_1$-$C_6$ alkyl, $C_2$-$C_6$ alkenyl, $C_2$-$C_6$ alkynyl, —$OR^{12}$, F, Cl, —$N_3$, —CN and —$N(R^{12})_2$, such that if $R^2$ is F or Cl, then $R^3$ is other than F or Cl;

$R^4$, $R^5$, $R^7$ and $R^8$ are each independently selected from H, $C_1$-$C_6$ alkyl, $C_1$-$C_6$ haloalkyl, $C_1$-$C_6$ hydroxyalkyl, halo, —$OR^{14}$, —$SR^{14}$ and —$N(R^{14})_2$;

$R^6$, $R^9$, $R^{10}$ and $R^{11}$ are each independently selected from H, $C_1$-$C_6$ alkyl, $C_2$-$C_6$ alkenyl, $C_2$-$C_6$ alkynyl, $C_3$-$C_7$ cycloalkyl, 5- or 6-membered monocyclic heteroaryl, 9- or 10-membered bicyclic heteroaryl, halo, —$OR^{14}$, —$SR^{14}$, —$S(O)R^{14}$, —$S(O)_2R^{14}$, —$S(O)_2N(R^{14})_2$, —$NHC(O)OR^{14}$, —$NHC(O)N(R^{14})_2$, $C_1$-$C_6$ haloalkyl, $C_1$-$C_6$ hydroxyalkyl, —O—($C_1$-$C_6$ haloalkyl), —CN, —$NO_2$, —$N(R^{14})_2$, —NH($C_1$-$C_6$ alkylene)-(5- or 6-membered monocyclic heteroaryl), —NH($C_1$-$C_6$ alkylene)-(9- or 10-membered bicyclic heteroaryl), —$C(O)R^{14}$, —$C(O)OR^{14}$, —$C(O)N(R^{14})_2$ and —$NHC(O)R^{14}$, wherein said $C_2$-$C_6$ alkenyl group and said $C_2$-$C_6$ alkynyl group may be optionally substituted with halo;

each occurrence of $R^{12}$ is independently selected from H, $C_1$-$C_6$ alkyl, —$C(O)R^{14}$ and —$C(O)OR^{14}$;

each occurrence of $R^{13}$ is independently selected from $C_1$-$C_6$ alkyl, $C_3$-$C_7$ cycloalkyl and $C_6$-$C_{10}$ aryl;

each occurrence of $R^{13}$ is independently selected from H, $C_1$-$C_6$ alkyl, $C_1$-$C_6$ haloalkyl, $C_1$-$C_6$ hydroxyalkyl, —($C_1$-$C_3$ alkylene)$_n$($C_3$-$C_7$ cycloalkyl), —($C_1$-$C_3$ alkylene)$_n$-($C_6$-$C_{10}$ aryl), —($C_1$-$C_3$ alkylene)$_n$-(4 to 7-membered heterocycloalkyl), —($C_1$-$C_3$ alkylene)$_n$-(5- or 6-membered monocyclic heteroaryl) and —($C_1$-$C_3$ alkylene)$_n$-(9- or 10-membered bicyclic heteroaryl);

m is 1, 2, 3, 4 or 5; and each occurrence of n is independently 0 or 1.

The Compounds of Formula (I) (also referred to herein as the "Cyclic Phosphate Substituted Nucleoside Compounds") and pharmaceutically acceptable salts thereof may be useful, for example, for inhibiting HCV viral replication or replicon activity, for inhibiting HCV NS5B activity, and for treating or preventing HCV infection in a patient. Without being bound by any specific theory, it is believed that the Cyclic Phosphate Substituted Nucleoside Compounds inhibit HCV viral replication by inhibiting HCV NS5B.

Accordingly, the present invention provides methods for treating or preventing HCV infection in a patient, comprising administering to the patient an effective amount of at least one Cyclic Phosphate Substituted Nucleoside Compound.

The details of the invention are set forth in the accompanying detailed description set forth below.

Other embodiments, aspects and features of the present invention are either further described in or will be apparent from the ensuing description, examples and appended claims.

DETAILED DESCRIPTION OF THE INVENTION

The present invention relates to Cyclic Phosphate Substituted Nucleoside Compounds, compositions comprising a Cyclic Phosphate Substituted Nucleoside Compound, and methods of using the Cyclic Phosphate Substituted Nucleoside Compounds for treating or preventing HCV infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein, refers to an amount of Cyclic Phosphate Substituted Nucleoside Compound and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HCV viral infection or HCV-virus related disorder, refers to reducing the likelihood or severity of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. In one embodiment, an aryl group can be optionally fused to a cycloalkyl or cycloalkanoyl group. Non-limiting examples of aryl groups include phenyl and naphthyl. In one embodiment, an aryl group is phenyl.

The term "cycloalkyl," as used herein, refers to a non-aromatic mono- or multicyclic ring system comprising from 3 to about 10 ring carbon atoms. In one embodiment, a cycloalkyl contains from about 5 to about 10 ring carbon atoms. In another embodiment, a cycloalkyl contains from 3 to about 7 ring atoms. In another embodiment, a cycloalkyl contains from about 5 to about 6 ring atoms. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. In one embodiment, a cycloalkyl group is unsubstituted. The term "3 to 6-membered cycloalkyl" refers to a cycloalkyl group having from 3 to 6 ring carbon atoms. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

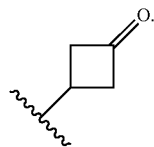 [SMILES: *C1CC(=O)C1]

The term "cycloalkylene," as used herein, refers to a cycloalkyl group, as defined above, wherein said cycloalkyl group has one or more endocyclic double bonds.

The term "halo," as used herein, means —F, —Cl, —Br or —I.

The term "haloalkyl," as used herein, refers to an alkyl group as defined above, wherein one or more of the alkyl group's hydrogen atoms have been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —CH$_2$F, —CHF$_2$, —CF$_3$, —CH$_2$Cl and —CCl$_3$. The term "C$_1$-C$_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —CH$_2$OH, —CH$_2$CH$_2$OH, —CH$_2$CH$_2$CH$_2$OH and —CH$_2$CH(OH)CH$_3$. The term "C$_1$-C$_6$ hydroxyalkyl" refers to a hydroxyalkyl group having from 1 to 6 carbon atoms.

The term "5 or 6-membered monocyclic heteroaryl," as used herein, refers to an aromatic monocyclic ring system comprising about 5 to about 6 ring atoms, wherein from 1 to 4 of the ring atoms is independently O, N or S and the remaining ring atoms are carbon atoms. A 5 or 6-membered monocyclic heteroaryl group is joined via a ring carbon atom, and any nitrogen atom of a heteroaryl can be optionally oxidized to the corresponding N-oxide. The term "5 or 6-membered monocyclic heteroaryl" also encompasses a 5 or 6-membered monocyclic heteroaryl group, as defined above, which is fused to a benzene ring. Non-limiting examples of 5 or 6-membered monocyclic heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, benzofurazanyl, indolyl, azaindolyl, benzimidazolyl, benzothienyl, imidazolyl, benzimidazolyl, thienopyridyl, thienopyrimidyl, pyrrolopyridyl, imidazopyridyl, isoquinolinyl, 1,2,4-triazinyl, benzothiazolyl and the like, and all isomeric forms thereof.

The term "9 or 10-membered bicyclic heteroaryl," as used herein, refers to an aromatic bicyclic ring system comprising about 9 to about 10 ring atoms, wherein from 1 to 4 of the ring atoms is independently O, N or S and the remaining ring atoms are carbon atoms. A 9 or 10-membered bicyclic heteroaryl group is joined via a ring carbon atom, and any nitrogen atom of a heteroaryl can be optionally oxidized to the corresponding N-oxide. Non-limiting examples of 9 or 10-membered bicyclic heteroaryls include imidazo[1,2-a]pyridinyl, imidazo[2,1-b]thiazolyl, benzofurazanyl, indolyl, azaindolyl, benzimidazolyl, benzothienyl, quinolinyl, benzimidazolyl, quinazolinyl, pyrrolopyridyl, imidazopyridyl, isoquinolinyl, benzoazaindolyl, benzothiazolyl, and the like, and all isomeric forms thereof.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from 3 to about 7 ring atoms. In another embodiment, a heterocycloalkyl group is monocyclic has from about 4 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

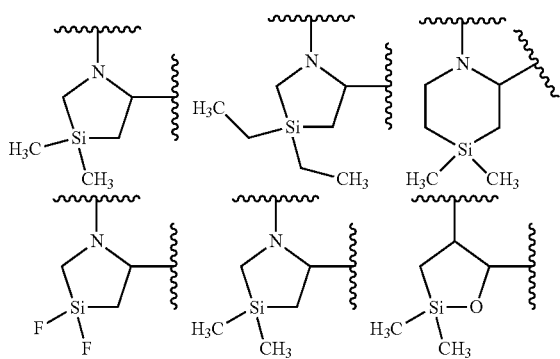

A ring carbon atom of a heterocycloalkyl group may be functionalized as a carbonyl group. An illustrative example of such a heterocycloalkyl group is:

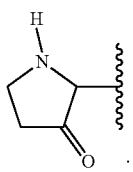

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., $C_1$-$C_6$ alkyl, $R^{12}$, m, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results directly from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Cyclic Phosphate Substituted Nucleoside Compound or a pharmaceutically acceptable salt of the compound. The transformation may occur by various mechanisms (e.g., by metabolic or chemical processes), such as, for example, through hydrolysis in blood.

For example, if a Cyclic Phosphate Substituted Nucleoside Compound or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkynl, N,N-di$(C_1-C_2)$alkylcarbamoyl-$(C_1-C_2)$alkyl and piperidino-, pyrrolidino- or morpholino$(C_2-C_3)$alkyl, and the like.

Similarly, if a Cyclic Phosphate Substituted Nucleoside Compound contains an alcohol functional group, a prodrug can be formed by the replacement of one or more of the hydrogen atoms of the alcohol groups with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate). Other non-limiting examples of alcohol-derived prodrugs include —P(O)(OH)$_2$; —P(O)(—O—$C_1-C_6$alkyl)$_2$; —P(O)(—NH—(α-aminoacyl group))(—O-aryl); —P(O)(—O—($C_1-C_6$ alkylene)-S-acyl)(—NH-arylalkyl); and those described in U.S. Pat. No. 7,879,815; International Publication Nos. WO2005/003047, WO2008/082602, WO2010/0081628, WO2010/075517 and WO2010/075549; Mehellou, *Chem. Med. Chem.*, 5:1841-1842 (2005); Bobeck et al., *Antiviral Therapy* 15:935-950 (2010); Furman et al., Future Medicinal Chemistry, 1:1429-1452 (2009); and Erion, *Microsomes and Drug Oxidations, Proceedings of the International Symposium*, 17th, Saratoga Springs, N.Y., United States, Jul. 6-10, 2008, 7-12 (2008).

If a Cyclic Phosphate Substituted Nucleoside Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$cycloalkyl, benzyl, a natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl; carboxy $(C_1-C_6)$alkyl; amino $(C_1-C_4)$alkyl or mono-N— or di-N,N—$(C_1-C_6)$alkylaminoalkyl; —C(Y$^4$)Y$^5$ wherein Y$^4$ is H or methyl and Y$^5$ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Cyclic Phosphate Substituted Nucleoside Compounds can form salts which are also within the scope of this invention. The term "salt(s)", as employed herein, denotes acidic salts formed with inorganic and/or organic acids, as well as basic salts formed with inorganic and/or organic bases. In addition, when a Cyclic Phosphate Substituted Nucleoside Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Cyclic Phosphate Substituted Nucleoside Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures may be separated into their individual diastereomers on the basis of their physical chemical differences by methods well-known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Cyclic Phosphate Substituted Nucleoside Compounds may be atropisomers (e.g., substituted biaryls) and are considered as part of this invention. Enantiomers can also be directly separated using chiral chromatographic techniques.

It is also possible that the Cyclic Phosphate Substituted Nucleoside Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Cyclic Phosphate Substituted Nucleoside Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, positional isomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) may be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Cyclic Phosphate Substituted Nucleoside Compounds, and of the salts, solvates, hydrates, esters and prodrugs of the Cyclic Phosphate Substituted Nucleoside Compounds, are intended to be included in the present invention.

The following abbreviations are used herein:
Ac acetyl
aq aqueous
Bn benzyl
Bu butyl
calc'd calculated
Celite/celite diatomaceous earth
DBU 1,8-diazabicyclo(5.4.0)undec-7-ene
DCM dichloromethane
DIPEA N,N-diisopropylethylamine
DMAP 4-dimethylaminopyridine
DMSO dimethyl sulfoxide
EDTA ethylenediamine tetraacetic acid
EGTA ethylene glycol-bis(β-aminoethyl ether)-N,N,N',N'-tetraacetic acid
Et ethyl
Et$_2$O diethyl ether
EtOH ethanol EtOAc ethyl acetate
Et$_3$N triethylamine
HPLC high-performance liquid chromatography
iPr isopropyl
iPrOH isopropanol
LC liquid chromatography
LC/MS liquid chromatography mass spectrometry
Me methyl
MeOH methanol
NMR nuclear magnetic resonance spectroscopy
NTP nucleoside triphosphate
obsv'd observed
Pd(OH)$_2$/C palladium hydroxide on carbon
Ph phenyl
Pr propyl
RT room temperature
Rt retention time
t-Bu tert-butyl
t-BuOOH tert-butyl peroxide
TFA trifluoroacetic acid
THF tetrahydrofuran
TLC thin layer chromatography The Compounds of Formula (I)

The present invention provides Cyclic Phosphate Substituted Nucleoside Compounds of Formula (I):

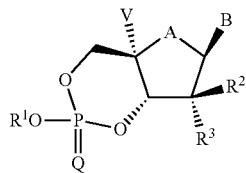

(I)

and pharmaceutically acceptable salts thereof, wherein A, B, R$^2$, R$^3$, Q and V are defined above for the Compounds of Formula (I).

In one embodiment, for the compounds of formula (I), A is O.

In another embodiment, for the compounds of formula (I), A is S.

In one embodiment, for the compounds of formula (I), Q is O.

In another embodiment, for the compounds of formula (I), Q is S.

In one embodiment, for the compounds of formula (I), R$^2$ is C$_1$-C$_3$ alkyl.

In another embodiment, for the compounds of formula (I), R$^2$ is —C≡CH.

In another embodiment, for the compounds of formula (I), R$^2$ is methyl.

In one embodiment, for the compounds of formula (I), R$^3$ is selected from —OH, F, Cl, —N$_3$, —CN, —C≡CH and —NH$_2$.

In another embodiment, for the compounds of formula (I), R$^3$ is selected from —OH, —Cl, —C≡CH and —NH$_2$.

In one embodiment, for the compounds of formula (I), R$^2$ is methyl and R$^3$ is selected from —OH, F, Cl, —N$_3$, —CN, —C≡CH and —NH$_2$.

In one embodiment, for the compounds of formula (I), B is selected from guanine, cytosine, adenine, uracil and

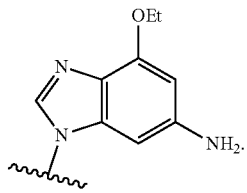 [SMILES: *n1cnc2c(OCC)cc(N)cc21]

In one embodiment, variables A, B, R$^1$, R$^2$, R$^3$, Q and V for the Compounds of Formula (I) are selected independently of each other.

In another embodiment, the Compounds of Formula (I) are in substantially purified form.

In one embodiment, the compounds of formula (I) have the formula (Ia):

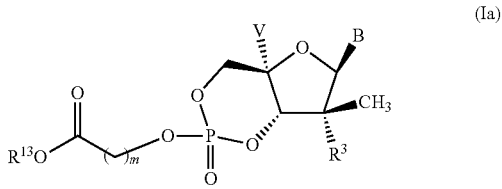

(Ia)

or a pharmaceutically acceptable salt thereof, wherein:
B is uracil, cytosine or:

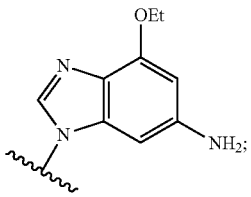 [SMILES: *n1cnc2c(OCC)cc(N)cc21]

R$^3$ is selected from —OH, F, Cl, N$_3$, —CN, C≡CH and —NH$_2$;
R$^{13}$ is C$_1$-C$_6$ alkyl or C$_3$-C$_7$ cycloalkyl; and
V is H or F; and
m is 1, 2, 3, 4 or 5.

In one embodiment, for the compounds of formula (I) or (Ia), B is uracil.

In one embodiment, for the compounds of formula (I) or (Ia), V is H.

In another embodiment, for the compounds of formula (I) or (Ia), V is F.

In one embodiment, for the compounds of formula (I) or (Ia), R$^3$ is F.

In another embodiment, for the compounds of formula (I) or (Ia), R$^3$ is Cl.

In still another embodiment, for the compounds of formula (I) or (Ia), R$^3$ is —C≡CH.

In another embodiment, for the compounds of formula (I) or (Ia), R$^3$ is —NH$_2$.

In one embodiment, for the compounds of formula (I) or (Ia), R$^{13}$ is C$_1$-C$_6$ alkyl.

In one embodiment, for the compounds of formula (I) or (Ia), R$^{13}$ is C$_3$-C$_7$ cycloalkyl.

In one embodiment, for the compounds of formula (I) or (Ia), R$^{13}$ is methyl, ethyl, isopropyl, n-butyl or cyclopentyl.

In one embodiment, for the compounds of formula (I) or (Ia), m is 1.

In another embodiment, for the compounds of formula (I) or (Ia), m is 2.

In another embodiment, for the compounds of formula (I) or (Ia), m is 3.

In still another embodiment, for the compounds of formula (I) or (Ia), m is 4.

In another embodiment, for the compounds of formula (I) or (Ia), m is 5.

In one embodiment, for the compounds of formula (I) or (Ia), m is 1 and $R^{13}$ is $C_1$-$C_6$ alkyl.

In another embodiment, for the compounds of formula (I) or (Ia), m is 2 and $R^{13}$ is $C_1$-$C_6$ alkyl.

In another embodiment, for the compounds of formula (I) or (Ia), m is 3 and $R^{13}$ is $C_1$-$C_6$ alkyl.

In still another embodiment, for the compounds of formula (I) or (Ia), m is 4 and $R^{13}$ is $C_1$-$C_6$ alkyl.

In another embodiment, for the compounds of formula (I) or (Ia), m is 5 and $R^{13}$ is $C_1$-$C_6$ alkyl.

In one embodiment, for the compounds of formula (I) or (Ia), m is 1 and $R^{13}$ is $C_3$-$C_7$ cycloalkyl.

In another embodiment, for the compounds of formula (I) or (Ia), m is 2 and $R^{13}$ is $C_3$-$C_7$ cycloalkyl.

In another embodiment, for the compounds of formula (I) or (Ia), m is 3 and $R^{13}$ is $C_3$-$C_7$ cycloalkyl.

In still another embodiment, for the compounds of formula (I) or (Ia), m is 4 and $R^{13}$ is $C_3$-$C_7$ cycloalkyl.

In another embodiment, for the compounds of formula (I) or (Ia), m is 5 and $R^{13}$ is $C_3$-$C_7$ cycloalkyl.

In one embodiment, for the compounds of formula (I) or (Ia), m is 1 and $R^{13}$ is isopropyl.

In another embodiment, for the compounds of formula (I) or (Ia), m is 2 and $R^{13}$ is isopropyl.

In another embodiment, for the compounds of formula (I) or (Ia), m is 3 and $R^{13}$ is selected from isopropyl, n-pentyl and cyclopentyl.

In still another embodiment, for the compounds of formula (I) or (Ia), m is 4 and $R^{13}$ is selected from methyl, ethyl, isopropyl, n-pentyl and cyclopentyl In another embodiment, for the compounds of formula (I) or (Ia), m is 5 and $R^{13}$ is isopropyl.

In one embodiment, variables B, $R^3$, $R^{13}$, V and m for the Compounds of Formula (Ia) are selected independently of each other.

In another embodiment, the Compounds of Formula (Ia) are in substantially purified form.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Other embodiments of the present invention include the following:

(a) A pharmaceutical composition comprising an effective amount of a Compound of Formula (I) or Formula (Ia) or a pharmaceutically acceptable salt thereof, and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of HCV protease inhibitors, HCV NS5B polymerase inhibitors and HCV NS5A inhibitors.

(d) A pharmaceutical combination that is (i) a Compound of Formula (I) and (ii) a second therapeutic agent selected from the group consisting of HCV antiviral agents, immunomodulators, and anti-infective agents; wherein the Compound of Formula (I) and the second therapeutic agent are each employed in an amount that renders the combination effective for inhibiting HCV replication, or for treating HCV infection and/or reducing the likelihood or severity of symptoms of HCV infection.

(e) The combination of (d), wherein the HCV antiviral agent is an antiviral selected from the group consisting of HCV protease inhibitors, HCV NS5B polymerase inhibitors and HCV NS5A inhibitors.

(f) A method of inhibiting HCV replication in a subject in need thereof which comprises administering to the subject an effective amount of a Compound of Formula (I).

(g) A method of treating HCV infection and/or reducing the likelihood or severity of symptoms of HCV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HCV antiviral agents, immunomodulators, and anti-infective agents.

(i) The method of (h), wherein the HCV antiviral agent is an antiviral selected from the group consisting of HCV protease inhibitors, HCV NS5B polymerase inhibitors and HCV NS5A inhibitors.

(j) A method of inhibiting HCV replication in a subject in need thereof which comprises administering to the subject the pharmaceutical composition of (a), (b) or (c) or the combination of (d) or (e).

(k) A method of treating HCV infection and/or reducing the likelihood or severity of symptoms of HCV infection in a subject in need thereof which comprises administering to the subject the pharmaceutical composition of (a), (b) or (c) or the combination of (d) or (e).

Additional embodiments of the invention include the pharmaceutical compositions, combinations and methods set forth in (a)-(k) above and the uses set forth in the discussion below, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

Non-limiting examples of the Compounds of Formula (I) include the compounds set forth in Table 1 in the Examples below and pharmaceutically acceptable salts thereof Methods for Making the Compounds of Formula
(I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes A, B and C below. Alternative synthetic pathways and analogous structures will be apparent to those skilled in the art of organic synthesis.

Scheme A shows a method useful for making nucleoside compounds of formula D, which correspond to the Compounds of Formula (I), wherein A is O; Q is O; and B, $R^1$, $R^2$ and $R^3$ are defined above for the Compounds of Formula (I).

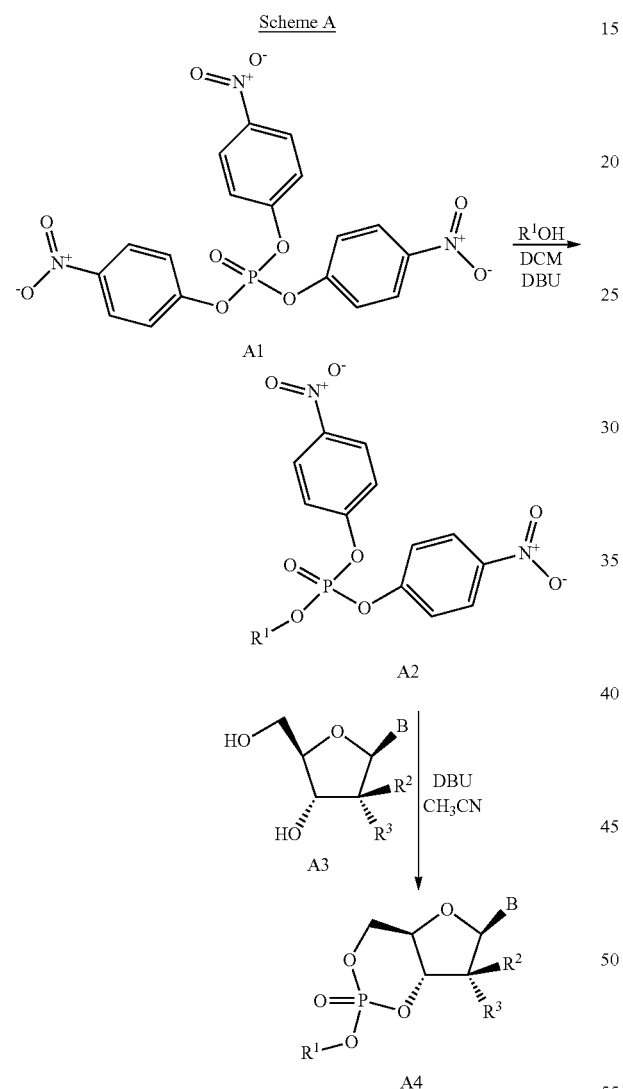

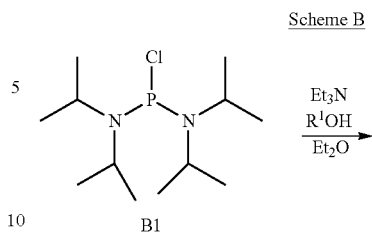

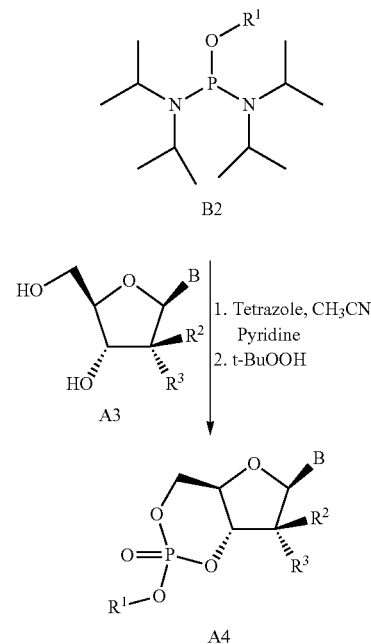

Tris(4-nitrophenyl) phosphate (A1) can be reacted with DBU and an alcohol of formula $R^1OH$ to provide a compound of formula A2. The compound of formula A2 is then reacted with a nucleoside of formula A3 to provide a cyclicphosphate nucleoside prodrug of formula A4.

Scheme B shows an alternate method useful for making nucleoside compounds of formula A4, which correspond to the Compounds of Formula (I), wherein A is O; Q is O; and B, $R^1$, $R^2$ and $R^3$ are defined above for the Compounds of Formula (I).

1-chloro-N,N,N',N'-tetraisopropylphosphinediamine (B1) can be reacted with triethylamine and an alcohol of formula $R^1OH$ to provide a compound of formula B2. The compound of formula B2 is then reacted with a nucleoside of formula A3 to provide a cyclic phosphate nucleoside prodrug of formula A4.

Scheme C shows an alternate method useful for making nucleoside compounds of formula C3, which correspond to the Compounds of Formula (I), wherein A is O or S; Q is U and B, $R^1$, $R^2$ and $R^3$ are defined above for the Compounds of Formula (I).

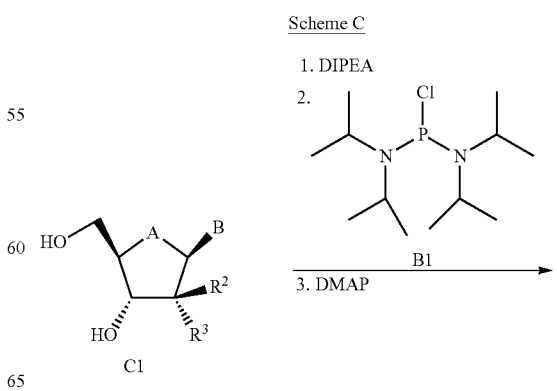

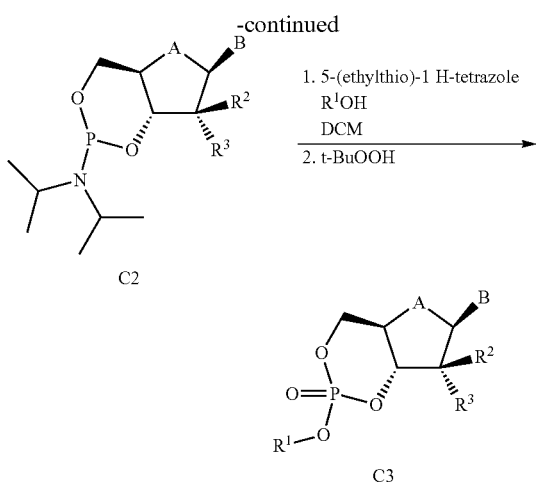

EXAMPLES

General Procedures

Reactions sensitive to moisture or air were performed under nitrogen or argon atmosphere using anhydrous solvents and reagents. The progress of reactions was determined using either analytical thin layer chromatography (TLC) usually performed with E. Merck pre-coated TLC plates, silica gel 60F-254, layer thickness 0.25 mm or liquid chromatography-mass spectrometry (LC-MS).

The analytical UPLC-MS system used consisted of a Waters SQD2 platform with electrospray ionization in positive and negative detection mode with an Acquity UPLC I-class solvent manager, column manager, sample manager and PDA detector. The column used for standard methods was a CORTECS UPLC C18 1.6 μm, 2.1×30 mm, and the column used for polars method was an ACQUITY UPLC HSST3 1.8 μm, 2.1×30 mm, the column temperature was 40° C., the flow rate was 0.7 mL/min, and injection volume was 1 μL. UV detection was in the range 210-400 nm. The mobile phase consisted of solvent A (water plus 0.05% formic acid) and solvent B (acetonitrile plus 0.05% formic acid) with different gradients for 4 different methods: 1/Starting with 99% solvent A for 0.2 minutes changing to 98% solvent B over 1 minutes, maintained for 0.4 minutes, then reverting to 99% solvent A over 0.1 minutes; 2/Starting with 99% solvent A for 0.5 minutes changing to 98% solvent B over 3.7 minutes, maintained for 0.4 minutes, then reverting to 99% solvent A over 0.1 minutes; 3/Starting with 100% solvent A for 0.4 minutes changing to 98% solvent B over 0.9 minutes, maintained for 0.3 minutes, then reverting to 100% solvent A over 0.1 minutes; 4/Starting with 100% solvent A for 0.8 minutes changing to 98% solvent B over 3.4 minutes, maintained for 0.4 minutes, then reverting to 100% solvent A over 0.1 minutes.

The analytical LC-MS system used consisted of a Agilent 6140 quadrupole LC/MS platform with electrospray ionization in positive and negative detection mode with an Agilent 1200 Series solvent manager, column manager, sample manager and PDA detector. The column for standard method was Purospher® STAR RP-18 endcapped 2 μm, Hibar® HR 50-2.1, the column temperature was 60° C., the flow rate was 0.8 mL/min, and injection volume was 0.5-5 μL. UV detection was in the range 210-400 nm. The mobile phase consisted of solvent A (water plus 0.05% formic acid) and solvent B (acetonitrile plus 0.05% formic acid) with different gradients for 2 different methods: 1) Starting with 98% solvent A changing to 100% solvent B over 1.8 minutes, maintained for 0.8 minutes; 2) Starting with 98% solvent A changing to 100% solvent B over 5.8 minutes, maintained for 0.3 minutes.

Preparative HPLC purifications were usually performed using a mass spectrometry directed system. Usually they were performed on a Waters Chromatography Workstation (MassLynx V4.1) configured with LC-MS System Consisting of: Waters ZQ™ 2000 (quad MS system with Electrospray Ionization), Waters 2545 Gradient Pump, Waters 2767 Injecto/Collector, Waters 2998 PDA Detector, the MS Conditions of: 100-1400 amu, Positive Electrospray, Collection Triggered by MS, and a Waters SUNFIRE® C-18 5 micron, 19 mm (id)×150 mm column. The mobile phases consisted of mixtures of acetonitrile (5-95%) in water containing 0.02% formic acid. Flow rates were maintained at 20 mL/min, the injection volume was 500 to 3000 μL, and the UV detection range was 210-400 nm. Mobile phase gradients were optimized for the individual compounds. Preparative HPLC were also performed on a Gilson system GX-281 (Trilution). The column was a Waters SUNFIRE® Prep C18 5 μm OBD, dimension 50×150 mm. The mobile phase consisted of acetonitrile (5-50%) in water containing 0.02% HCOOH over 60 minutes. Flow rates were maintained at 117 mL/min, the injection volume was 1000 to 7000 μL, and the UV detection range was 260 nm.

Reactions performed using microwave irradiation were normally carried out using an Emrys Optimizer manufactured by Personal Chemistry, or an Initiator manufactured by Biotage. Concentration of solutions was carried out on a rotary evaporator in vacuo. Flash chromatography was usually performed using a Biotage® Flash Chromatography apparatus (Isolera) on silica gel (15-45μ, 40-63μ, or spheric silica) in pre-packed cartridges of the size noted. $^1$H NMR spectra were acquired at 400 MHz or 500 MHz spectrometers in CDCl$_3$ solutions unless otherwise noted Chemical shifts were reported in parts per million (ppm). Tetramethylsilane (TMS) was used as internal reference in CDCl$_3$ solutions, and residual CH$_3$OH peak or TMS was used as internal reference in CD$_3$OD solutions. Coupling constants (J) were reported in hertz (Hz). Chiral analytical chromatography was performed on one of CHIRALPAK® AS, CHIRALPAK®AD, CHIRALCEL® OD, CHIRALCEL® IA, or CHIRALCEL® OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of CHIRALPAK AS, of CHIRALPAK AD, CHIRALCEL® OD, CHIRALCEL®IA, CHIRALCEL® OJ columns (20×250 mm) (Daicel Chemical Industries, Ltd.) with desired isocratic solvent systems identified on chiral analytical chromatography or by supercritical fluid (SFC) conditions.

Example 1

Preparation of Intermediate Compounds A, B and C

Scheme 1

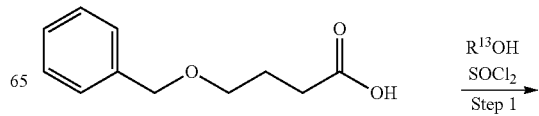

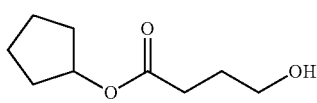

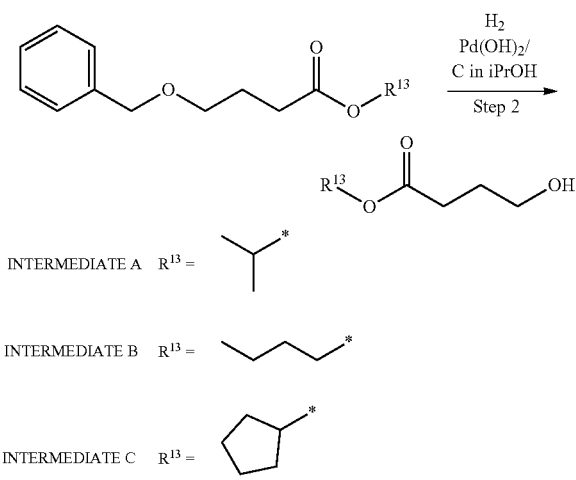

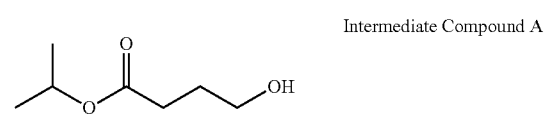

Intermediate Compound A

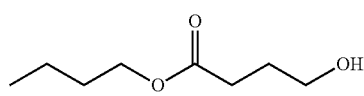

Step 1: To a solution of 4-(benzyloxy)butanoic acid (22.8 g, 117 mmol) in propan-2-ol (250 mL) at 0° C. was added thionyl chloride (10.25 mL, 141 mmol), dropwise. The reaction reaction was heated to 100° C. and allowed to stir at this temperature for 7 hours, then cooled to room temperature and allowed to stir at this temperature overnight. The reaction mixture was concentrated in vacuo and used directly in the next step without further purification.

Step 2: To a solution of isopropyl 4-(benzyloxy)butanoate (14.68 g, 62.1 mmol) in propan-2-ol (180 mL) was added palladium hydroxide on carbon (2.9 g, 20.65 mmol). The reaction was subjected to three cycles of vacuum/nitrogen purge, then allowed to stir under hydrogen at room temperature overnight. The resulting mixture was filtered through pad of celite and $K_2CO_3$, and the filtrate was concentrated in vacuo to provide intermediate compound A as an oil. $^1$H NMR (400 MHz, CDCl$_3$) δ 4.99 (heptuplet, J=6.24 Hz, 1H), 3.66 (t, J=6.18 Hz, 2H), 2.38 (t, J=7.12 Hz, 2H), 1.89-1.82 (m, 2H), 1.22 (d, J=6.24 Hz, 6H).

Intermediate Compound B

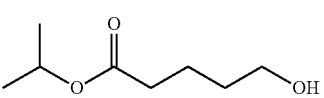

Intermediate compound B was made using the method described above for the synthesis intermediate compound A and substituting 1-butanol for propan-2-ol in Step 1. $^1$H NMR (400 MHz, CDCl$_3$) δ 4.09 (t, J=6.69 Hz, 2H), 3.69 (t, J=6.14 Hz, 2H), 2.44 (t, J=7.09 Hz, 2H), 1.92-1.86 (m, 2H), 1.65-1.58 (m, 2H), 1.43-1.34 (m, 2H), 0.94 (t, J=7.40 Hz, 3H).

Intermediate Compound C

Intermediate compound C was made using the method described above for the synthesis intermediate compound A and substituting cyclopentanol for propan-2-ol in Step 1. $^1$H NMR (400 MHz, CDCl$_3$) δ 5.19-5.15 (m, 1H), 3.69 (d, J=6.15 Hz, 2H), 2.40 (t, J=7.10 Hz, 2H), 1.91-1.57 (m, 10H).

Example 2

Preparation of Intermediate Compounds D, E, F and G

Scheme 2

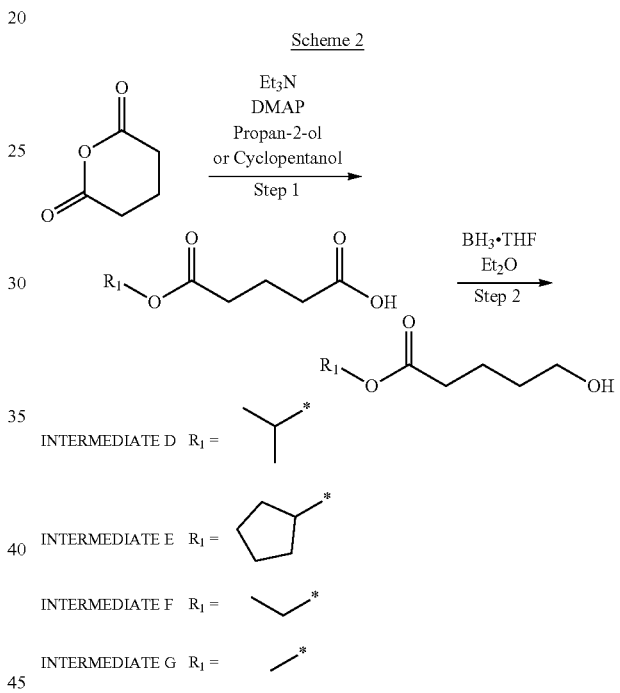

Intermediate Compound D

Step 1: To a solution of glutaric anhydride (13 g, 114.0 mmol) and DMAP (1.39 g, 11.39 mmol) in propan-2-ol (165 mL) at room temperature was added triethylamine (15.86 mL, 114.0 mmol). The reaction mixture was allowed to stir at 95° C. overnight, then concentrated in vacuo. The crude residue obtained obtained was dissolved in EtOAc and the organic layer was washed with a 1M citric acid solution (twice) and then with brine. The organic layer was then dried, filtered and concentrated in vacuo, and the product obtained was dried in vacuo, then used directly in the next step: LC/MS: [(M+1)]$^+$=175.0.

Step 2: To 0° C. solution of 5-isopropoxy-5-oxopentanoic acid (18.65 g, 107.0 mmol) in diethyl ether (234 mL) under nitrogen, was added borane tetrahydrofuran complex (107.0 mL, 107.0 mmol), dropwise. The reaction was allowed to stir at room temperature for 90 minutes, then the reaction mixture was slowly added at 0° C. to a saturated aqueous NaHCO₃ solution. The aqueous layer was extracted with diethyl ether (2×200 mL and the combined organic extracts were combined were dried, filtered and concentrated in vacuo (bath temperature=20° C.)). The crude residue obtained obtained was partitioned between water and DCM. The organic layer was dried, filtered, concentrated in vacuo (bath temperature=20° C.) and dried in vacuo. The crude residue obtained obtained was purified using flash chromatography on silica gel (DCM/MeOH) to provide intermediate compound D. $^1$H NMR (400 MHz, DMSO-$d_6$) δ 4.89 (heptuplet, J=6.24 Hz, 1H), 4.38 (t, J=5.20 Hz, 1H), 3.40-3.35 (m, 2H), 2.26-2.22 (m, 2H), 1.57-1.50 (m, 2H), 1.44-1.37 (m, 2H), 1.17 (d, J=6.24 Hz, 6H); LC/MS: $[(M+1)]^+=$161.2.

Intermediate Compound E

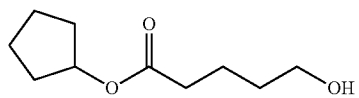

Intermediate compound E was made using the method described above for the synthesis intermediate compound D and substituting cyclopentanol for propan-2-ol in Step 1. $^1$H NMR (400 MHz, DMSO-$d_6$) δ 5.08-5.03 (m, 1H), 4.39 (t, J=5.12 Hz, 1H), 3.40-3.36 (m, 2H), 2.24 (t, J=7.31 Hz, 2H), 1.86-1.77 (m, 2H), 1.65-1.37 (m, 10H); LC/MS: $[(M+1)]^+=$187.2.

Intermediate Compound F

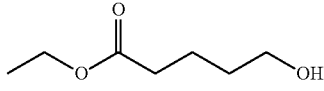

Intermediate compound F was made using the method described above for the synthesis intermediate compound D and substituting ethanol for propan-2-ol in Step 1. $^1$H NMR (400 MHz, DMSO-$d_6$) δ 4.39 (t, J=5.17 Hz, 1H), 4.04 (q, J=7.08 Hz, 2H), 3.40-3.36 (m, 2H), 2.28 (t, J=7.35 Hz, 2H), 1.58-1.51 (m, 2H), 1.44-1.37 (m, 2H), 1.17 (t, J=7.08 Hz, 3H); LC/MS: $[(M+1)]^+=$147.0.

Intermediate Compound G

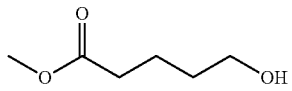

Intermediate compound G was made using the method described above for the synthesis intermediate compound D and substituting methanol for propan-2-ol in Step 1. $^1$H NMR (400 MHz, DMSO-$d_6$) δ 4.39 (t, J=5.17 Hz, 1H), 3.58 (s, 3H), 3.40-3.36 (m, 2H), 2.30 (t, J=7.35 Hz, 2H), 1.59-1.51 (m, 2H), 1.44-1.37 (m, 2H); LC/MS: $[(M+1)]^+=$133.2.

Example 2

Preparation of Intermediate Compound H

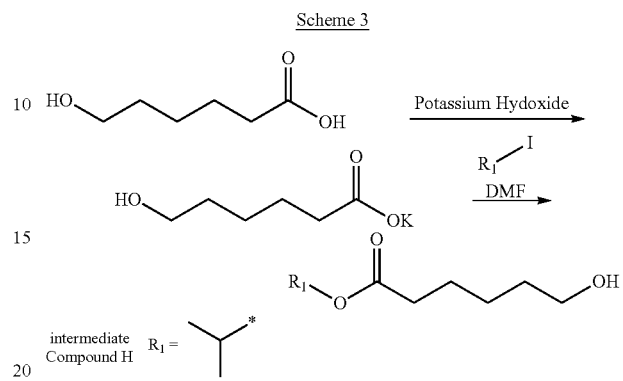

Step 1: A solution of 6-hydroxyhexanoic acid (5 g, 37.8 mmol) in 1M aqueous potassium hydroxide solution (37.8 mL, 37.8 mmol) was allowed to stir at room temperature for 2 hours. The reaction mixture was concentrated in vacuo and the crude residue obtained obtained was triturated in diethyl ether, filtered and the solid was washed with diethyl ether. The solid was then dried in vacuo over $P_2O_5$ at 40° C. to provide potassium 6-hydroxyhexanoate.

Step 2: To a solution of potassium 6-hydroxyhexanoate (3 g, 17.62 mmol) in DMF (25 mL) was added dropwise 2-iodopropane (2.11 mL, 21.15 mmol) at room temperature under nitrogen. The reaction was allowed to stir at room temperature overnight, then the reaction mixture was diluted with EtOAc. The collected organic layer was washed with a metabisulfite solution and brine, then dried, filtered and concentrated in vacuo. The crude residue obtained was purified using flash chromatography on silica gel (DCM/MeOH: 0 to 8%) to provide the intermediate compound H. $^1$H NMR (400 MHz, CDCl₃) δ 5.01 (heptuplet, J=6.20 Hz, 1H), 3.65 (t, J=6.58 Hz, 2H), 2.28 (t, J=7.42 Hz, 2H), 1.69-1.56 (m, 4H), 1.44-1.36 (m, 2H), 1.23 (d, J=6.20 Hz, 6H).

Example 3

Preparation of Intermediate Compound I

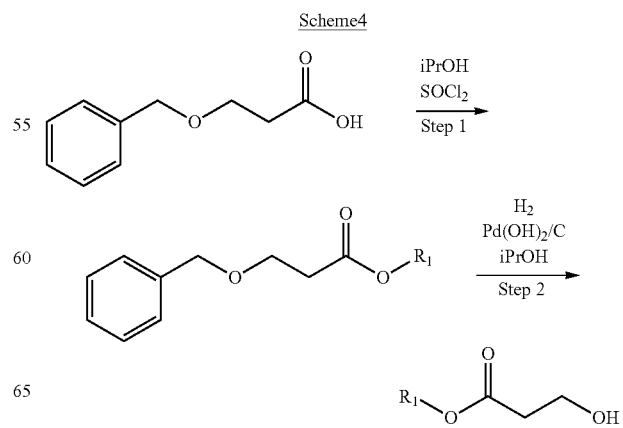

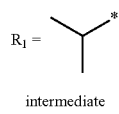

intermediate compound I

Intermediate compound I was made using the methods described in Example 1, Steps 1 and 2. Step 1 was carried out using 3-(benzyloxy)propanoic acid as starting material and isopropanol in place of propan-2-ol. Step 2 was carried out at room temperature for 4 days. $^1$H NMR (400 MHz, DMSO-$d_6$) δ 4.89 (heptuplet, J=6.27 Hz, 1H), 4.64 (brs, 1H), 3.62 (t, J=6.19 Hz, 2H), 2.38 (t, J=6.19 Hz, 2H), 1.18 (d, J=6.27 Hz, 6H).

Example 4

Preparation of Intermediate Compound J

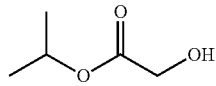

Intermediate Compound J

Intermediate Compound J is commercially available.

Example 5

Preparation of Intermediate Compound L

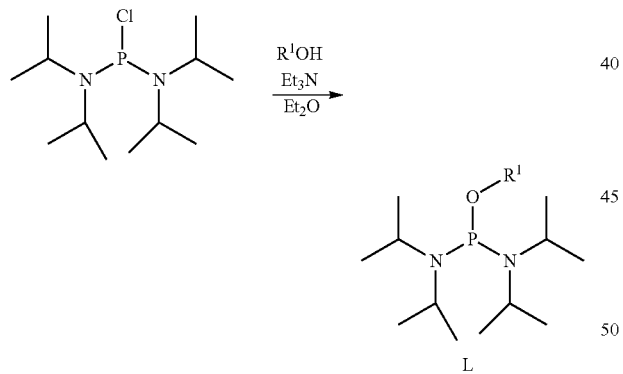

L

To a cold −15° C. solution of 1-chloro-N,N,N′,N′-tetraisopropylphosphinediamine (1 eq., 5.0 g, 18.74 mmol) in diethyl ether (96 mL, 5.1 mL/mmol) were added triethylamine (3 eq., 7.83 mL, 56.2 mmol) under nitrogen. To the resulting solution was slowly added a solution of appropriate intermediate compound (1 eq., 2.74 g, 18.74 mmol) in diethyl ether (48 mL, 2.6 mL/mmol). The reaction was allowed to stir at −15° C. for 1 hour and then at room temperature for 2 hours. The resulting suspension was filtered under nitrogen and washed with diethyl ether. The filtrate was concentrated in vacuo at room temperature under nitrogen to provide intermediate compound L, which was stored at −20° C. under nitrogen and used without further purification: $^{31}$P NMR (162 MHz, CDCl$_3$) δ 123.9 (s, 1P).

Example 6

General Method A For the Preparation of Compounds of the Invention

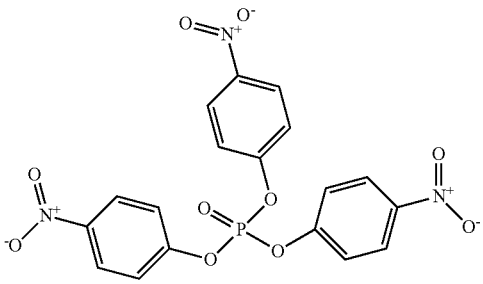

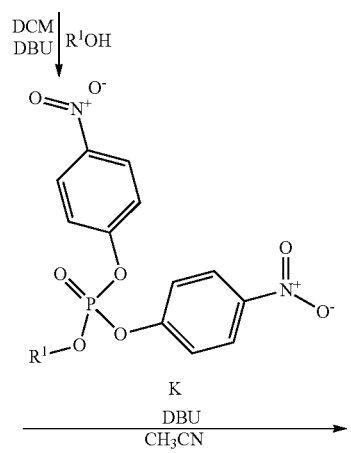

K

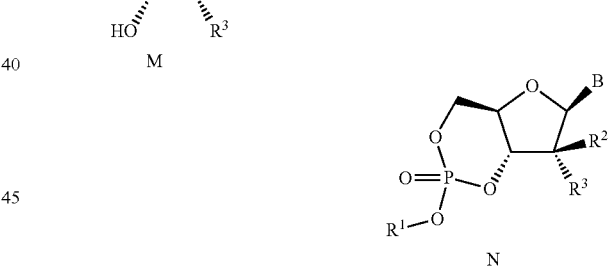

N

Step 1—Preparation of a Compound of Formula K: To a solution of an alcohol of formula R$^1$OH (1.2 eq.) and tris(4-nitrophenyl) phosphate (1.1 eq.) in DCM (45 mL) at 0° C. under N$_2$ is added dropwise 1,8-diazabicyclo[5.4.0]undec-7-ene (DBU, 1.0 eq.). The cold bath is removed and the reaction is allowed to stir for 3 hours, during which time the reaction temperature went from 0° C. to room temperature. The reaction is then allowed to stir at room temperature overnight.

Step 2—reparation of a Compound of Formula N: The reaction mixture from step 1 is added dropwise to a solution of a nucleoside of formula M (1.0 eq.) and DBU (2.5 eq.) in acetonitrile (6.4 mL)/THF (6.4 mL)/DCM (6.4 mL) at room temperature. The resulting reaction is then allowed to stir at room temperature overnight, and then concentrated in vacuo. The crude residue obtained is dissolved in DCM and the mixture is washed with a saturated NaHCO$_3$ solution, and brine. The organic layer is dried and concentrated in vacuo and the crude residue obtained is purified using flash chromatography on silica gel (DCM/MeOH) to provide 2 mixtures of separated diastereoisomeric intermediates (on the phosphorus atom). Each diasteromeric mixture is then further purified using preparative HPLC (C18, H₂O/ CH₃CN) to provide each separate phosphorus diasteromer of the compound of formula N.

Example 7

General Method B For the Preparation of Compounds of the Invention

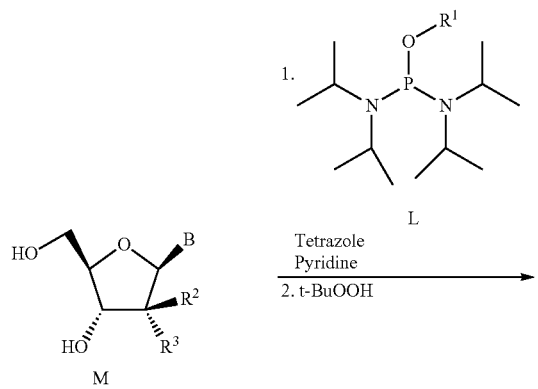

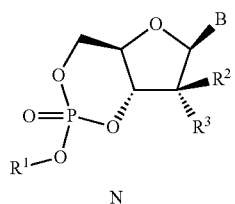

To a solution of appropriate nucleoside starting material (1.0 eq.) in pyridine (6.7 mL per mole of starting material) is added 1H-tetrazole 0.45 M in CH₃CN (3.0 eq). The reaction mixture is cooled to −5° C., and a solution of intermediate compound of formula L (1.1 eq.) in acetonitrile (3.3 mL per mole of L) is added dropwise. The reaction is allowed to stir at −5° C. for 1.5 hours, then at room temperature for 2 hours. A solution of tert-butylhydroperoxide, 5M in decane (2.5 eq.) is then added dropwise, and the resulting reaction mixture is allowed to stir for 20 minutes at room temperature. The reaction mixture is concentrated in vacuo and co-evaporated with toluene (2×) and the crude residue obtained is purified using flash chromatography on silica gel (DCM/MeOH: 0 to 10%) to provide a mixture of diastereoisomers. The mixture of diastereoisomers can be further purified using preparative HPLC (C18, H₂O/CH₃CN: 0 to 50%) or using MS-preparative HPLC to provide the 2 isolated diasteromers of the product of formula N.

Example 8

General Method C For the Preparation of Compounds of the Invention

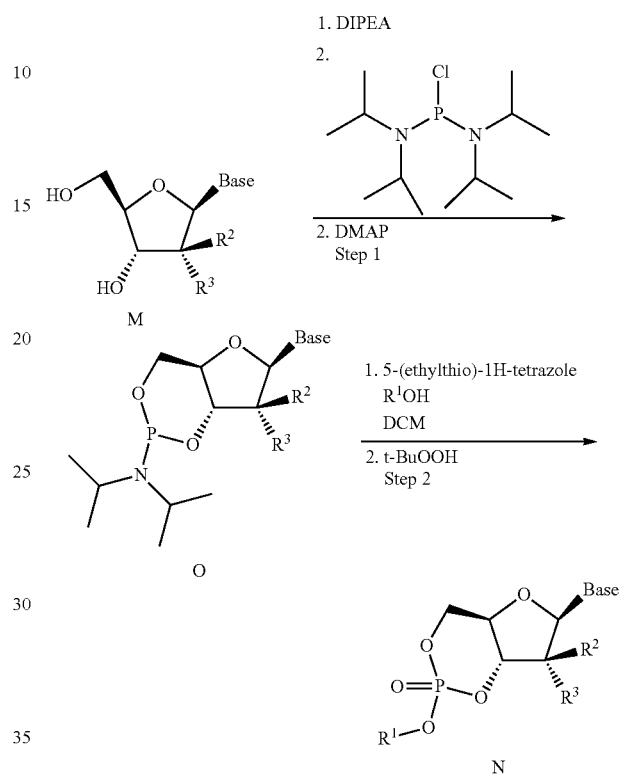

Step 1: To a 0° C. solution of a nucleoside of formula M (1 eq.) and DIPEA (3 eq.) in anhydrous DCM (10 mL per mmol of M) is added 1-chloro-N,N,N',N'-tetraisopropylphosphin-ediamine (1.2 eq). The reaction is allowed to stir at 0° C. for 30 minutes and then at room temperature for an additional 3 hours. The reaction can be monitored using ³¹P NMR in CD₃CN. N,N-dimethylpyridin-4-amine (0.5 eq.) is then added, and the reaction is allowed to stir at room temperature overnight. The reaction mixture is filtered and concentrated in vacuo and the crude residue obtained is dissolved in acetone and then filtered. The filtrate is then concentrated in vacuo under nitrogen to provide the intermediate compound of formula O.

Step 2: To a solution of intermediate compound O in DCM (50 mL) at 0° C. under nitrogen is added 5-(ethylthio)-1H-tetrazole (1.5 eq.) followed by the corresponding intermediate compound (1.5 eq.). The reaction is allowed to stir at 0° C. for 15 minutes then at room temperature for 3 hours. Tert-butylhydroperoxide 5M in decane (3 eq.) is then added and the reaction mixture is allowed to stir at room temperature overnight. The reaction mixture is then washed with 1N HCl and brine, and the organic layer is extracted and concentrated in vacuo. The crude residue obtained is then purified using flash chromatography on silica gel (DCM/MeOH: 0 to 5%) to provide the 2 separated diastereoisomers in protected form.

To a solution of each protected diastereoisomer in DCM (5 mL per mmol of diasteromer) at room temperature is added TFA (32 eq.). The reaction is allowed to stir at room temperature for 1 hour, and then concentrated in vacuo. The crude residue obtained is dissolved in DCM/MeOH and the TFA salts were neutralized by passing the resulting solution through a 5 g cartridge of polymer-bound $HCO_3$. The filtrate is then concentrated in vacuo and the crude residue obtained is purified using preparative HPLC (C18, $H_2O/CH_3CN$) followed by flash chromatography on silica gel (DCM/MeOH) to provide each pure diasteromer of the compound of formula N.

The compounds of the invention, set forth in Table 1 below, were prepared as a mixture of phosphorus diasteromers using general method A, B or C as described above in Examples 6, 7 and 8, respectively. The diasteromeric mixtures obtained were separated using either Preparative-HPLC, MS-preparative HPLC or preparative Chiral-HPLC. The column having the heading "INT" provides the intermediate compound numbers that represent the intermediate that was coupled with the appropriate nucleoside to make each exemplified compound. The column having the heading "METHOD" provides the general method used to make each exemplified compound.

TABLE 1

| Cpd No. | STRUCTURE | NMR $^1$H (ppm) | NMR $^{31}$P (ppm) | Stereo P | LC/MS $(M + 1)^+$ | INT | METHOD |
|---|---|---|---|---|---|---|---|
| 1A | 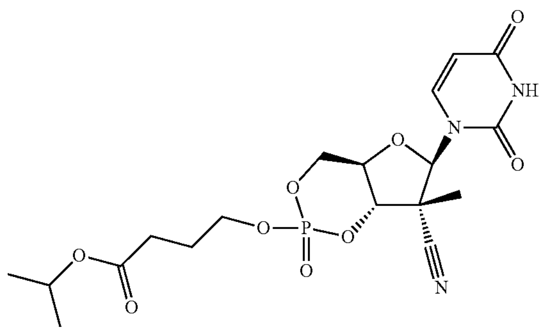 | DMSO: 11.70 (1H, s), 7.80 (1H, d, J = 8.2 Hz), 6.49 (1H, s), 5.74 (1H, d, J = 8.1 Hz), 4.95-4.85 (1H, m), 4.70 (1H, ddt, J = 4.9, 10.4, 11.0 Hz), 4.57 (2H, dd, J = 9.5, 20.4 Hz), 4.25-4.10 (3H, m), 2.42 (2H, dd, J = 7.4, 7.4 Hz), 1.99-1.90 (2H, m), 1.35 (3H, s), 1.18 (6H, d, J = 6.2 Hz) | DMSO: −7.31 | $S_P$ | 458.1 | A | A |
| 1B | 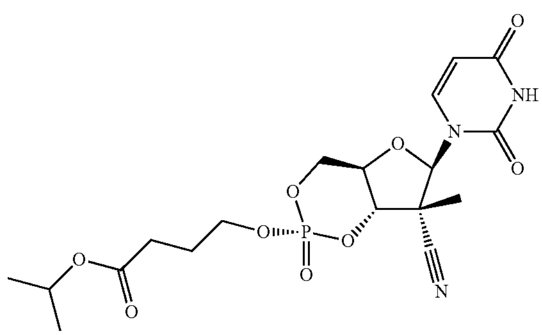 [SMILES: CC(C)OC(=O)CCCO[P@]1(=O)OC[C@H]2O[C@@H](n3ccc(=O)[nH]c3=O)[C@](C)(C#N)[C@@H]2O1] | DMSO: 11.68 (1H, s), 7.80 (1H, d, J = 8.2 Hz), 6.49 (1H, s), 5.71 (1H, d, J = 8.1 Hz), 4.93-4.86 (2H, m), 4.78-4.66 (2H, m), 4.38-4.30 (1H, m), 4.13 (2H, dd, J = 6.5, 14.1 Hz), 2.37 (2H, dd, J = 7.4, 7.4 Hz), 1.95-1.86 (2H, m), 1.34 (3H, s), 1.18 (6H, d, J = 6.3 Hz); $^{31}$P NMR (DMSO, 161.98 MHz) | DMSO: −6.00 | $R_P$ | 458.2 | A | A |
| 2A | 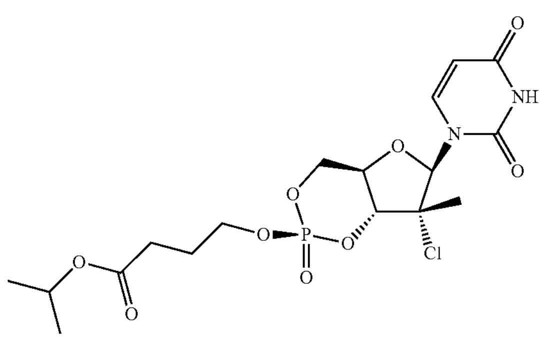 [SMILES: CC(C)OC(=O)CCCO[P@@]1(=O)OC[C@H]2O[C@@H](n3ccc(=O)[nH]c3=O)[C@](C)(Cl)[C@@H]2O1] | | DMSO: −6.90 | $S_P$ | 467.0 | A | A |

TABLE 1-continued

| Cpd No. | STRUCTURE | NMR $^1$H (ppm) | NMR $^{31}$P (ppm) | Stereo P | LC/MS (M + 1)$^+$ | INT | METHOD |
|---|---|---|---|---|---|---|---|
| 2B | 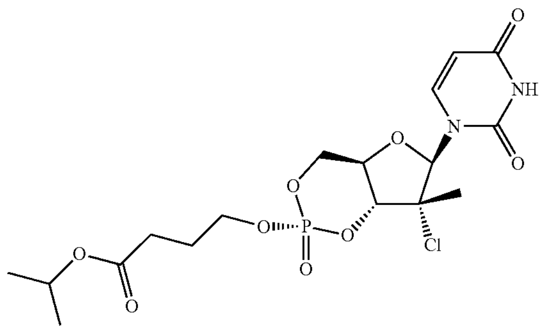 [SMILES: CC(C)OC(=O)CCCO[P@]1(=O)OC[C@H]2O[C@@H](n3ccc(=O)[nH]c3=O)[C@](C)(Cl)[C@@H]2O1] | | DMSO: −5.83 | R$_P$ | 467.0 | A | A |
| 3A | 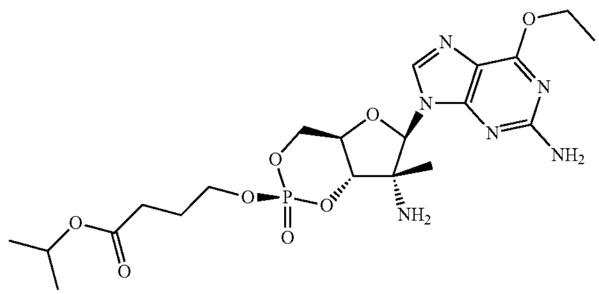 [SMILES: CCOc1nc(N)nc2c1ncn2[C@@H]1O[C@@H]2CO[P@](=O)(OCCCC(=O)OC(C)C)O[C@H]2[C@@]1(C)N] | | DMSO: −5.68 | S$_P$ | 515.2 | A | A |
| 3B | 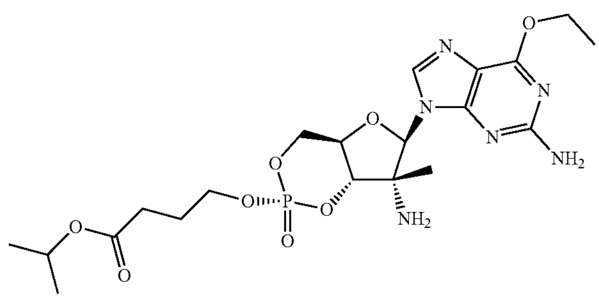 [SMILES: CCOc1nc(N)nc2c1ncn2[C@@H]1O[C@@H]2CO[P@@](=O)(OCCCC(=O)OC(C)C)O[C@H]2[C@@]1(C)N] | | DMSO: −4.74 | R$_P$ | 515.2 | A | A |
| 4A | 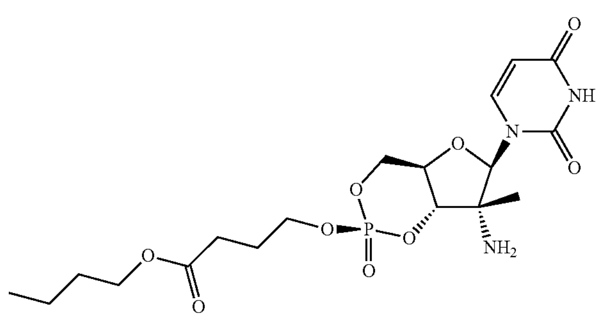 [SMILES: CCCCOC(=O)CCCO[P@@]1(=O)OC[C@H]2O[C@@H](n3ccc(=O)[nH]c3=O)[C@](C)(N)[C@@H]2O1] | | DMSO: −5.93 | S$_P$ | 462.2 | B | A |
| 4B | 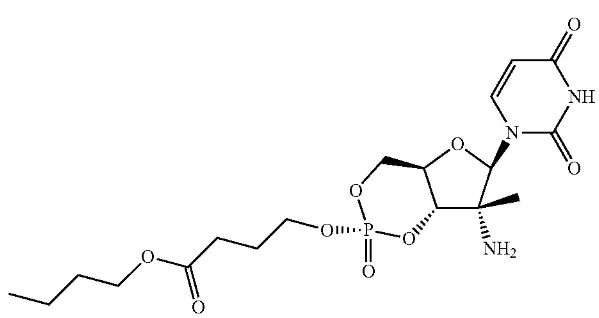 [SMILES: CCCCOC(=O)CCCO[P@]1(=O)OC[C@H]2O[C@@H](n3ccc(=O)[nH]c3=O)[C@](C)(N)[C@@H]2O1] | | DMSO: −4.68 | R$_P$ | 462.2 | B | A |

TABLE 1-continued

| Cpd No. | STRUCTURE | NMR $^1$H (ppm) | NMR $^{31}$P (ppm) | Stereo P | LC/MS (M + 1)$^+$ | INT | METHOD |
|---|---|---|---|---|---|---|---|
| 5A | 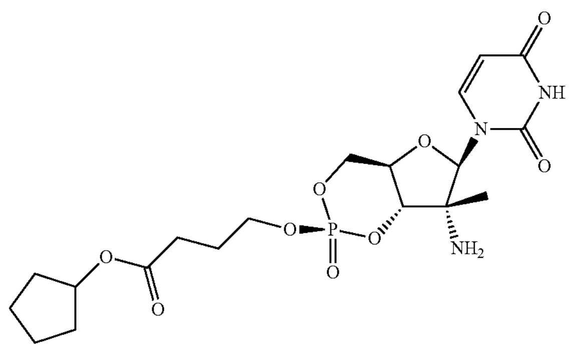 [SMILES: C[C@@]1(N)[C@@H]2O[P@@](=O)(OCCCC(=O)OC3CCCC3)OC[C@H]2O[C@H]1n1ccc(=O)[nH]c1=O] | | DMSO: -5.92 | S$_P$ | 474.2 | C | A |
| 5B | 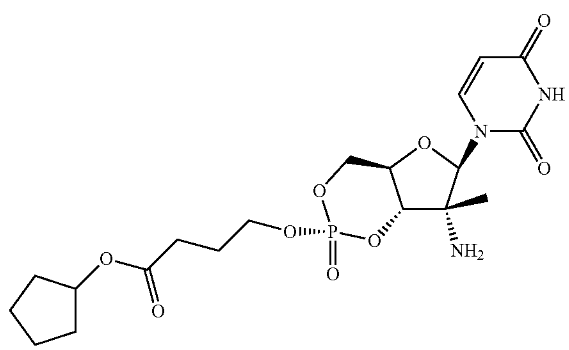 [SMILES: C[C@@]1(N)[C@@H]2O[P@](=O)(OCCCC(=O)OC3CCCC3)OC[C@H]2O[C@H]1n1ccc(=O)[nH]c1=O] | | DMSO: -4.66 | R$_P$ | 474.2 | C | A |
| 6A | 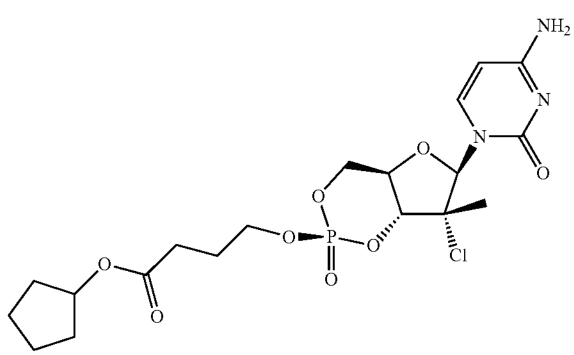 [SMILES: C[C@@]1(Cl)[C@@H]2O[P@@](=O)(OCCCC(=O)OC3CCCC3)OC[C@H]2O[C@H]1n1ccc(N)nc1=O] | | DMSO: -6.83 | S$_P$ | 492.2 | C | A |
| 6B | 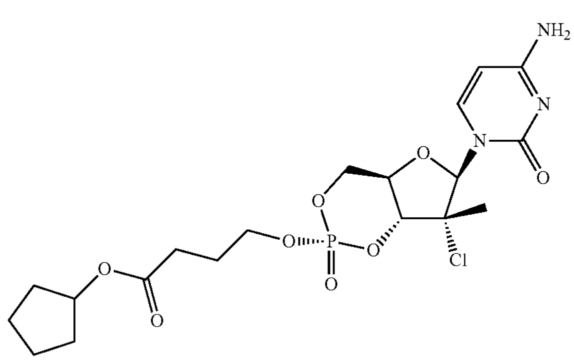 [SMILES: C[C@@]1(Cl)[C@@H]2O[P@](=O)(OCCCC(=O)OC3CCCC3)OC[C@H]2O[C@H]1n1ccc(N)nc1=O] | | DMSO: -5.73 | R$_P$ | 492.3 | C | A |

TABLE 1-continued

| Cpd No. | STRUCTURE | NMR $^1$H (ppm) | NMR $^{31}$P (ppm) | Stereo P | LC/MS (M + 1)$^+$ | INT | METHOD |
|---|---|---|---|---|---|---|---|
| 7A or 7B | 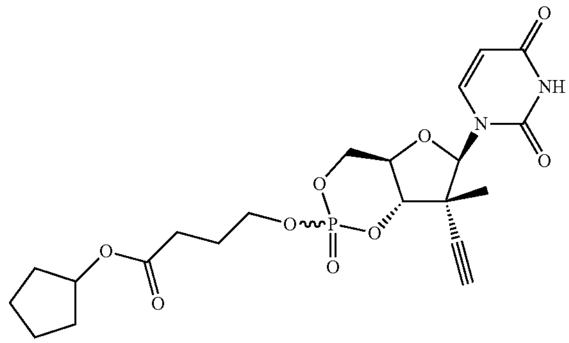 | | DMSO: −5.58 | S$_P$ or R$_P$ | 483.2 | C | A |
| 8A | 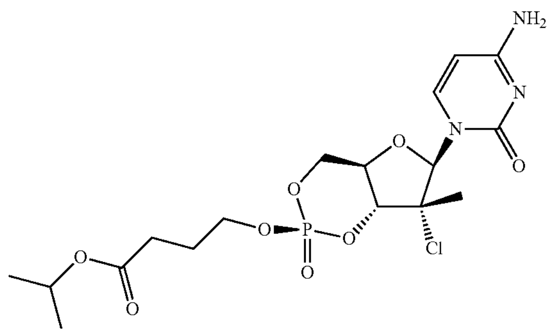 [SMILES: CC(C)OC(=O)CCCO[P@@]1(=O)OC[C@H]2O[C@@H](n3ccc(N)nc3=O)[C@](C)(Cl)[C@@H]2O1] | DMSO: 7.67 (d, J = 7.58 Hz, 1H), 7.41 (brs, 2H), 6.51 (s, 1H), 5.81 (d, J = 7.58 Hz, 1H), 4.89 (heptuplet, J = 6.24 Hz, 1H), 4.75-4.62 (m, 2H), 4.34 (d, J = 9.84 Hz, 1H), 4.25-4.19 (m, 1H), 4.15-4.10 (m, 2H), 2.42 (t, J = 7.19 Hz, 2H), 1.97-1.91 (m, 2H), 1.45 (s, 3H), 1.18 (d, J = 6.24 Hz, 6H) | DMSO: −6.83 | S$_P$ | 466.0 | A | A |
| 8B | 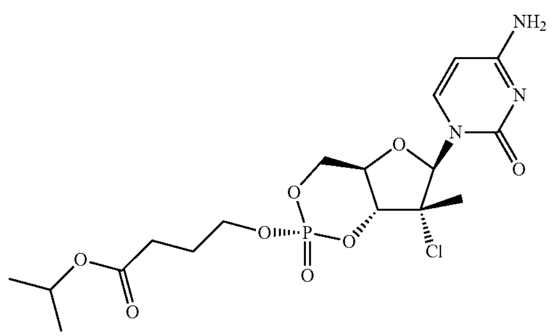 [SMILES: CC(C)OC(=O)CCCO[P@]1(=O)OC[C@H]2O[C@@H](n3ccc(N)nc3=O)[C@](C)(Cl)[C@@H]2O1] | DMSO: 7.69 (d, J = 7.51 Hz, 1H), 7.39 (brs, 2H), 6.53 (s, 1H), 5.77 (d, J = 7.51 Hz, 1H), 4.90 (heptuplet, J = 6.23 Hz, 1H), 4.77-4.70 (m, 3H), 4.41-4.35 (m, 1H), 4.14-4.09 (m, 2H), 2.37 (t, J = 7.19 Hz, 2H), 1.93-1.86 (m, 2H), 1.43 (s, 3H), 1.18 (d, J = 6.23 Hz, 6H) | DMSO: −5.73 | R$_P$ | 466.0 | A | A |
| 9A | 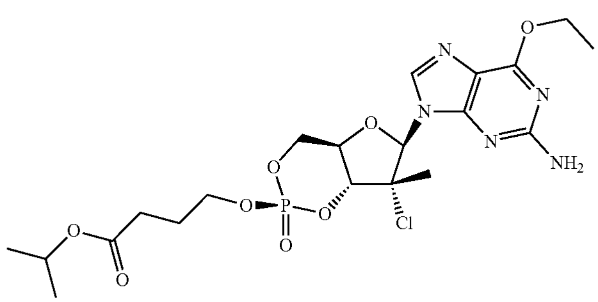 [SMILES: CCOc1nc(N)nc2c1ncn2[C@@H]1O[C@@H]2CO[P@](=O)(OCCCC(=O)OC(C)C)O[C@H]2[C@@]1(C)Cl] | DMSO: 8.17 (s, 1H), 6.52 (s, 1H), 6.50 (brs, 2H), 4.89-4.78 (m, 2H), 4.74-4.65 (m, 1H), 4.45 (q, J = 6.93 Hz, 2H), 4.34-4.28 (m, 1H), 4.18-4.13 (m, 2H), 2.41 (t, J = 7.25 Hz, 2H), 1.98-1.91 (m, 2H), 1.38-1.34 (m, 6H), 1.15-1.12 (m, 6H) | DMSO: −6.57 | S$_P$ | 534.3 | A | A |

TABLE 1-continued

| Cpd No. | STRUCTURE | NMR $^1$H (ppm) | NMR $^{31}$P (ppm) | Stereo P | LC/MS (M + 1)$^+$ | INT | METHOD |
|---|---|---|---|---|---|---|---|
| 9B | 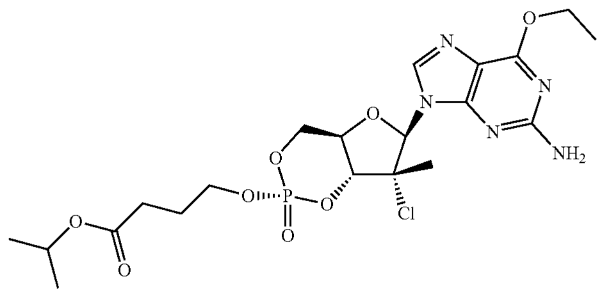 [SMILES: CCOc1nc(N)nc2c1ncn2[C@@H]1O[C@@H]2CO[P@@](=O)(OCCCC(=O)OC(C)C)O[C@H]2[C@@]1(C)Cl] | DMSO: 8.18 (s, 1H), 6.61 (brs, 2H), 6.51 (s, 1H), 4.90 (heptuplet, J = 6.26 Hz, 1H), 4.79-4.69 (m, 2H), 4.52-4.48 (m, 1H), 4.45 (q, J = 7.04 Hz, 2H), 4.16-4.10 (m, 2H), 2.39 (t, J = 7.30 Hz, 2H), 1.94-1.87 (m, 2H), 1.38-1.34 (m, 6H), 1.19 (d, J = 6.26 Hz, 6H) | DMSO: −5.81 | R$_P$ | 534.3 | A | A |
| 10A | 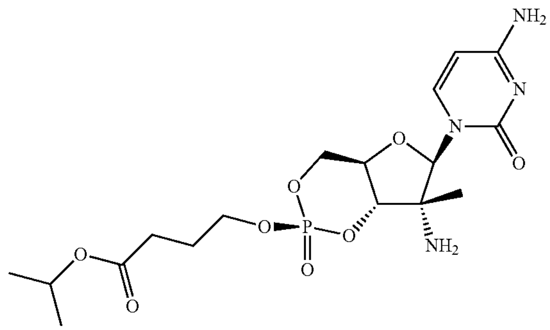 [SMILES: CC(C)OC(=O)CCCO[P@@]1(=O)OC[C@H]2O[C@@H](n3ccc(N)nc3=O)[C@](C)(N)[C@@H]2O1] | DMSO: 7.63 (d, J = 7.44 Hz, 1H), 7.28-7.23 (m, 2H), 5.95 (s, 1H), 5.77-5.76 (m, 1H), 4.89 (heptuplet, J = 6.28 Hz, 1H), 4.68-4.59 (m, 1H), 4.56-4.51 (m, 1H), 4.28-4.22 (m, 1H), 4.10-4.01 (m, 3H), 2.41 (t, J = 7.32 Hz, 2H), 1.96-1.89 (m, 4H), 1.17 (d, J = 6.28 Hz, 6H), 0.95 (brs, 3H) | DMSO: −5.90 | S$_P$ | 447.4 | A | A |
| 10B | 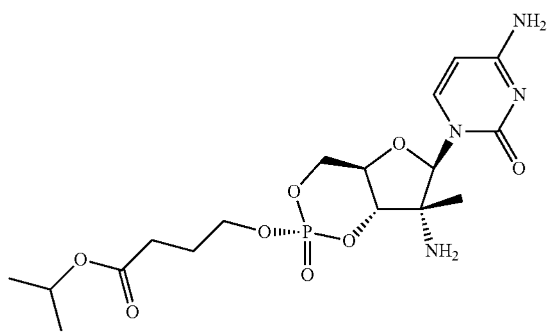 | DMSO: 7.67 (d, J = 7.49 Hz, 1H), 7.26-7.21 (m, 2H), 5.97 (s, 1H), 5.74 (d, J = 7.49 Hz, 1H), 4.90 (heptuplet, J = 6.28 Hz, 1H), 4.68-4.58 (m, 2H), 4.43-4.32 (m, 2H), 4.11-4.06 (m, 2H), 2.37 (t, J = 7.35 Hz, 2H), 1.95-1.84 (m, 4H), 1.19 (d, J = 6.28 Hz, 6H), 0.95 (brs, 3H) | DMSO: −4.60 | R$_P$ | 447.4 | A | A |
| 11A | 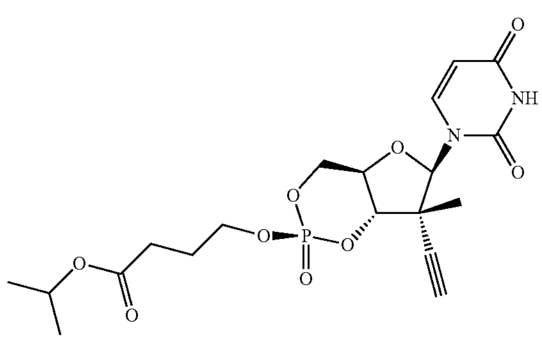 [SMILES: C#C[C@]1(C)[C@@H]2O[P@@](=O)(OCCCC(=O)OC(C)C)OC[C@H]2O[C@H]1n1ccc(=O)[nH]c1=O] | DMSO: 11.61 (1H, s), 7.78 (1H, d, J = 8.1 Hz), 6.28 (1H, s), 5.68 (1H, d, J = 8.1 Hz), 4.95-4.84 (1H, m), 4.72-4.61 (2H, m), 4.25 (1H, d, J = 9.5 Hz), 4.18-4.08 (3H, m), 3.65 (1H, s), 2.42 (2H, dd, J = 7.3, 7.3 Hz), 1.98-1.90 (2H, m), 1.20-1.17 (9H, m) | DMSO: −6.67 | S$_P$ | 457.0 | A | A |

TABLE 1-continued

| Cpd No. | STRUCTURE | NMR $^1$H (ppm) | NMR $^{31}$P (ppm) | Stereo P | LC/MS (M + 1)$^+$ | INT | METHOD |
|---|---|---|---|---|---|---|---|
| 11B | 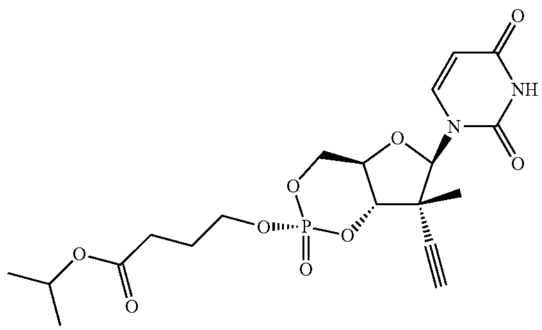 [SMILES: C#C[C@]1(C)[C@@H]2O[P@](=O)(OCCCC(=O)OC(C)C)OC[C@H]2O[C@H]1n1ccc(=O)[nH]c1=O] | DMSO) 11.59 (1H, s), 7.81 (1H, d, J = 8.1 Hz), 6.29 (1H, s), 5.66 (1H, dd, J = 2.1, 8.2 Hz), 4.95-4.85 (1H, m), 4.74-4.62 (3H, m), 4.34-4.26 (1H, m), 4.14-4.07 (2H, m), 3.61 (1H, s), 2.37 (2H, dd, J = 7.4, 7.4 Hz), 1.94-1.85 (2H, m), 1.20-1.17 (9H, m); | DMSO: −5.59 | $R_P$ | 457.0 | A | A |
| 12A | 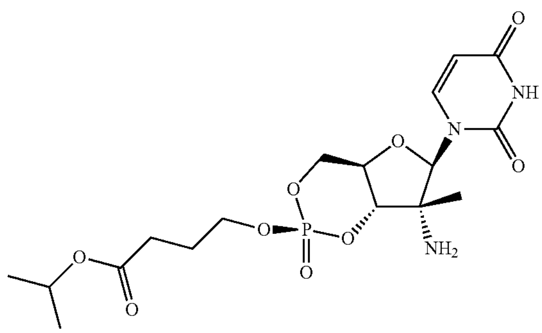 | DMSO: 11.50 (1H, s), 7.75 (1H, d, J = 8.1 Hz), 5.89 (1H, s), 5.65 (1H, d, J = 8.1 Hz), 4.94-4.84 (1H, m), 4.69-4.53 (2H, m), 4.30-4.22 (1H, m), 4.14-4.04 (3H, m), 2.41 (2H, dd, J = 7.3, 7.3 Hz), 2.02 (2H, s), 1.97-1.88 (2H, m), 1.18 (6H, d, J = 6.3 Hz), 1.01 (3H, s) | DMSO: −5.92 | $S_P$ | 448.0 | A | A |
| 12B | 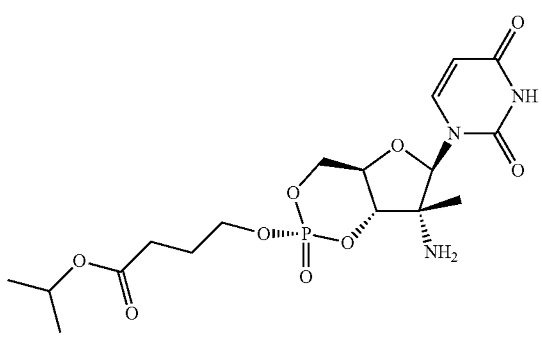 | DMSO: 11.48 (1H, s), 7.78 (1H, d, J = 8.1 Hz), 5.90 (1H, s), 5.62 (1H, d, J = 8.1 Hz), 4.95-4.85 (1H, m), 4.67-4.60 (2H, m), 4.48-4.37 (2H, m), 4.12-4.05 (2H, m), 2.37 (2H, dd, J = 7.4, 7.4 Hz), 2.00 (2H, s), 1.92-1.83 (2H, m), 1.19 (6H, d, J = 6.3 Hz), 1.01 (3H, s) | DMSO: −4.66 | $R_P$ | 448.2 | A | A |
| 13A | 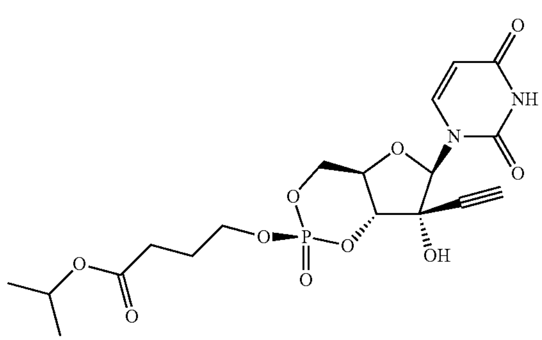 [SMILES: C#C[C@@]1(O)[C@@H]2O[P@@](=O)(OCCCC(=O)OC(C)C)OC[C@H]2O[C@H]1n1ccc(=O)[nH]c1=O] | DMSO: 11.54 (1H, s), 7.79 (1H, d, J = 8.2 Hz), 7.18 (1H, s), 6.05 (1H, s), 5.67 (1H, dd, J = 0.9, 6.7 Hz), 4.94-4.87 (1H, m), 4.68 (1H, dd, J = 4.2, 9.3 Hz), 4.64-4.57 (1H, m), 4.38 (1H, d, J = 9.7 Hz), 4.15-4.07 (3H, m), 3.79 (1H, s), 2.46-2.39 (2H, m), 2.00-1.91 (2H, m), 1.19 (6H, d, J = 6.3 Hz) | DMSO: −6.37 | $S_P$ | 459.0 | A | B |

TABLE 1-continued

| Cpd No. | STRUCTURE | NMR $^1$H (ppm) | NMR $^{31}$P (ppm) | Stereo P | LC/MS (M + 1)$^+$ | INT | METHOD |
|---|---|---|---|---|---|---|---|
| 13B | 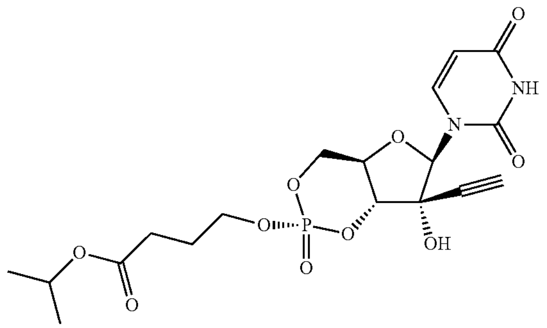 [SMILES: C#C[C@@]1(O)[C@@H]2O[P@](=O)(OCCCC(=O)OC(C)C)OC[C@H]2O[C@H]1n1ccc(=O)[nH]c1=O] | DMSO: 11.51 (1H, s), 7.84 (1H, d, J = 8.1 Hz), 7.13 (1H, s), 6.06 (1H, s), 5.64 (1H, d, J = 8.1 Hz), 4.94-4.86 (1H, m), 4.75 (1H, d, J = 9.8 Hz), 4.70-4.62 (2H, m), 4.30-4.22 (1H, m), 4.12-4.06 (2H, m), 3.83 (1H, s), 2.38-2.32 (2H, m), 1.92-1.84 (2H, m), 1.19 (6H, d, J = 6.2 Hz) | DMSO: −5.20 | R$_P$ | 459.0 | A | B |
| 14A | 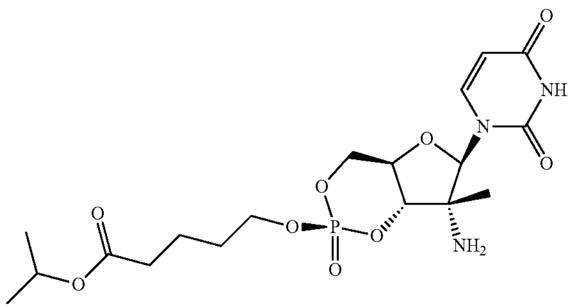 [SMILES: CC(C)OC(=O)CCCCO[P@@]1(=O)OC[C@H]2O[C@@H](n3ccc(=O)[nH]c3=O)[C@](C)(N)[C@@H]2O1] | DMSO: 11.49 (1H, s), 7.72 (1H, d, J = 7.9 Hz), 5.89 (1H, s), 5.64 (1H, dd, J = 1.2, 8.0 Hz), 4.93-4.83 (1H, m), 4.66-4.53 (2H, m), 4.30-4.22 (1H, m), 4.10-4.03 (3H, m), 2.30 (2H, t, J = 7.3 Hz), 2.01 (2H, s), 1.72-1.58 (4H, m), 1.17 (6H, dd, J = 0.9, 6.3 Hz), 1.01 (3H, s) | DMSO: −5.90 | S$_P$ | 462.3 | D | A |
| 14B | 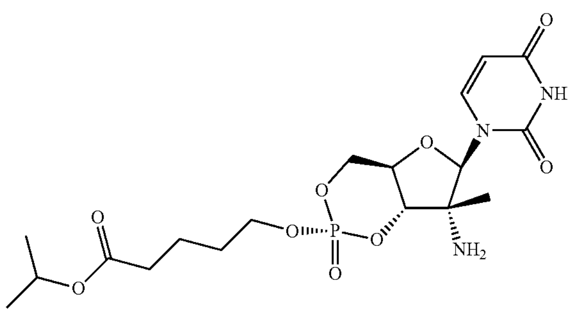 [SMILES: CC(C)OC(=O)CCCCO[P@]1(=O)OC[C@H]2O[C@@H](n3ccc(=O)[nH]c3=O)[C@](C)(N)[C@@H]2O1] | DMSO: 11.46 (1H, s), 7.78 (1H, d, J = 8.1 Hz), 5.90 (1H, s), 5.61 (1H, d, J = 8.1 Hz), 4.94-4.84 (1H, m), 4.67-4.60 (2H, m), 4.47-4.34 (2H, m), 4.10-4.03 (2H, m), 2.30 (2H, t, J = 7.0 Hz), 2.00 (2H, s), 1.66-1.55 (4H, m), 1.18 (6H, d, J = 6.3 Hz), 1.02 (3H, s) | DMSO: −4.63 | R$_P$ | 462.1 | D | A |
| 15A | 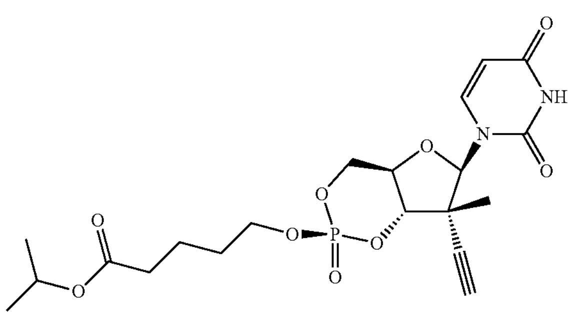 [SMILES: C#C[C@]1(C)[C@@H]2O[P@@](=O)(OCCCCC(=O)OC(C)C)OC[C@H]2O[C@H]1n1ccc(=O)[nH]c1=O] | DMSO: 11.58 (1H, s), 7.77 (1H, d, J = 8.1 Hz), 6.27 (1H, s), 5.67 (1H, d, J = 8.1 Hz), 4.93-4.83 (1H, m), 4.70-4.60 (2H, m), 4.25-4.05 (4H, m), 3.63 (1H, s), 2.34-2.28 (2H, m), 1.73-1.58 (4H, m), 1.18-1.16 (9H, m) | DMSO: −6.66 | S$_P$ | 471.2 | D | A |
| 15B | 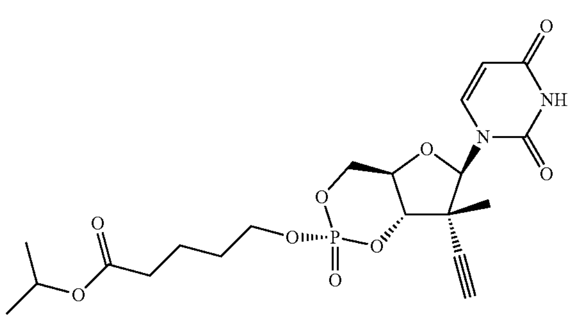 [SMILES: C#C[C@]1(C)[C@@H]2O[P@](=O)(OCCCCC(=O)OC(C)C)OC[C@H]2O[C@H]1n1ccc(=O)[nH]c1=O] | DMSO: 11.57 (1H, s), 7.80 (1H, d, J = 8.2 Hz), 6.29 (1H, s), 5.65 (1H, dd, J = 2.2, 8.1 Hz), 4.92-4.85 (1H, m), 4.74-4.60 (3H, m), 4.33-4.25 (1H, m), 4.11-4.05 (2H, m), 3.60 (1H, s), 2.30 (2H, dd, J = 7.2, 7.2 Hz), 1.68-1.56 (4H, m), 1.18 (9H, d, J = 6.2 Hz) | DMSO: −5.56 | R$_P$ | 471.0 | D | A |

TABLE 1-continued

| Cpd No. | STRUCTURE | NMR ¹H (ppm) | NMR ³¹P (ppm) | Stereo P | LC/MS (M + 1)⁺ | INT | METHOD |
|---|---|---|---|---|---|---|---|
| 16A | 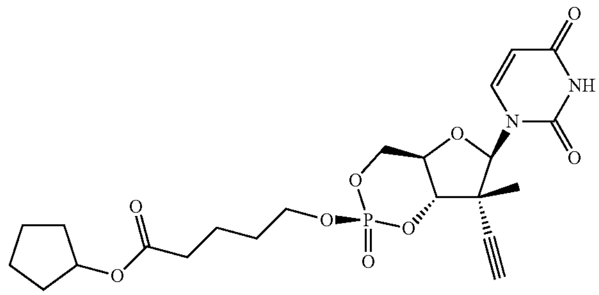 [SMILES: C#C[C@]1(C)[C@@H]2O[P@@](=O)(OCCCCC(=O)OC3CCCC3)OC[C@H]2O[C@H]1n1ccc(=O)[nH]c1=O] | DMSO: 11.58 (1H, s), 7.76 (1H, d, J = 8.1 Hz), 6.27 (1H, s), 5.67 (1H, d, J = 8.1 Hz), 5.08-5.03 (1H, m), 4.70-4.60 (2H, m), 4.22 (1H, d, J = 8.6 Hz), 4.18-4.06 (3H, m), 3.63 (1H, s), 2.31 (2H, dd, J = 7.2, 7.2 Hz), 1.85-1.76 (2H, m), 1.74-1.50 (10H, m), 1.17 (3H, s) | DMSO: −6.65 | $S_P$ | 497.2 | E | A |
| 16B | 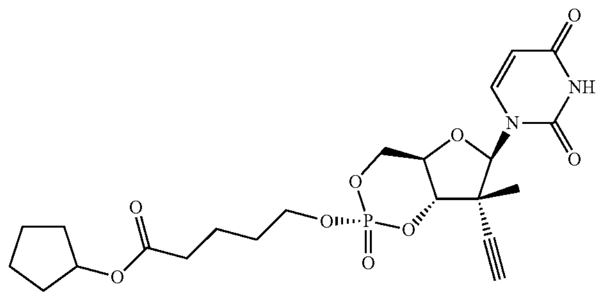 [SMILES: C#C[C@]1(C)[C@@H]2O[P@](=O)(OCCCCC(=O)OC3CCCC3)OC[C@H]2O[C@H]1n1ccc(=O)[nH]c1=O] | DMSO: 11.56 (1H, s), 7.80 (1H, d, J = 8.2 Hz), 6.29 (1H, s), 5.65 (1H, d, J = 8.1 Hz), 5.10-5.04 (1H, m), 4.74-4.60 (3H, m), 4.34-4.25 (1H, m), 4.12-4.05 (2H, m), 3.60 (1H, s), 2.30 (2H, dd, J = 7.1, 7.1 Hz), 1.86-1.77 (2H, m), 1.68-1.52 (10H, m), 1.18 (3H, s) | DMSO: −5.56 | $R_P$ | 497.2 | E | A |
| 17A | 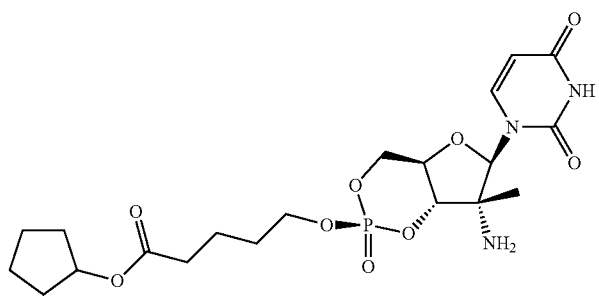 [SMILES: C[C@@]1(N)[C@@H]2O[P@@](=O)(OCCCCC(=O)OC3CCCC3)OC[C@H]2O[C@H]1n1ccc(=O)[nH]c1=O] | | DMSO: −5.91 | $S_P$ | 488.6 | E | A |
| 17B | 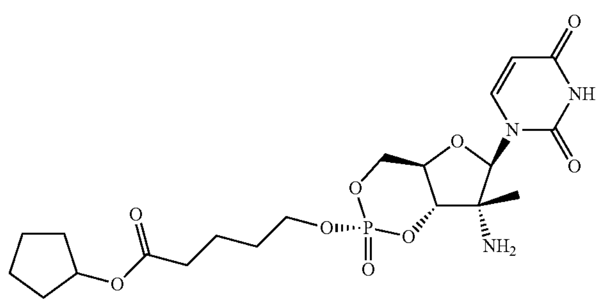 [SMILES: C[C@@]1(N)[C@@H]2O[P@](=O)(OCCCCC(=O)OC3CCCC3)OC[C@H]2O[C@H]1n1ccc(=O)[nH]c1=O] | | DMSO: −4.63 | $R_P$ | 488.2 | E | A |
| 18A | 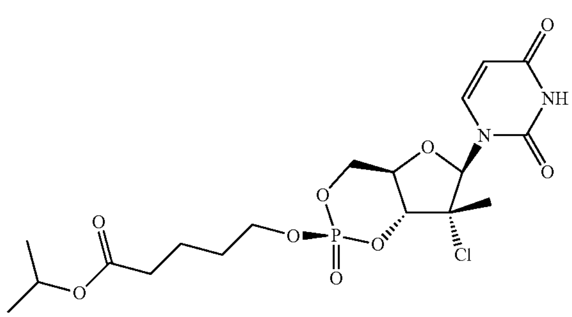 [SMILES: CC(C)OC(=O)CCCCO[P@@]1(=O)OC[C@H]2O[C@@H](n3ccc(=O)[nH]c3=O)[C@](C)(Cl)[C@@H]2O1] | DMSO: 11.63 (1H, s), 7.77 (1H, d, J = 8.1 Hz), 6.43 (1H, s), 5.70 (1H, d, J = 8.1 Hz), 4.93-4.83 (1H, m), 4.73-4.63 (2H, m), 4.44 (1H, d, J = 9.5 Hz), 4.27-4.08 (3H, m), 2.31 (2H, dd, J = 7.2, 7.2 Hz), 1.74-1.58 (4H, m), 1.52 (3H, s), 1.17 (6H, d, J = 6.3 Hz) | DMSO: −6.84 | $S_P$ | 481.0 | D | A |

TABLE 1-continued

| Cpd No. | STRUCTURE | NMR $^1$H (ppm) | NMR $^{31}$P (ppm) | Stereo P | LC/MS (M + 1)$^+$ | INT | METHOD |
|---|---|---|---|---|---|---|---|
| 18B | 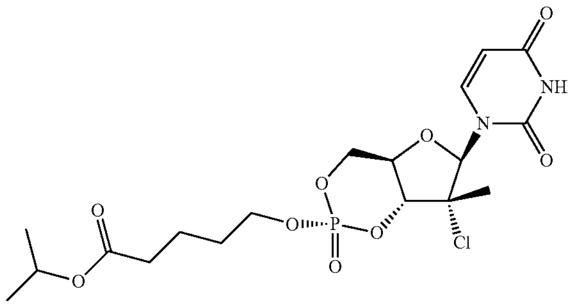 [SMILES: CC(C)OC(=O)CCCCO[P@]1(=O)OC[C@H]2O[C@@H](n3ccc(=O)[nH]c3=O)[C@](C)(Cl)[C@@H]2O1] | DMSO: 11.64-11.60 (1H, m), 7.80 (1H, d, J = 8.1 Hz), 6.45 (1H, s), 5.68 (1H, d, J = 8.1 Hz), 4.93-4.85 (2H, m), 4.76-4.70 (2H, m), 4.38 (1H, dd, J = 9.3, 16.1 Hz), 4.14-4.07 (2H, m), 2.30 (2H, dd, J = 7.1, 7.1 Hz), 1.68-1.57 (4H, m), 1.52 (3H, s), 1.18 (6H, d, J = 6.3 Hz) | DMSO: −5.74 | R$_P$ | 481.0 | D | A |
| 19A | 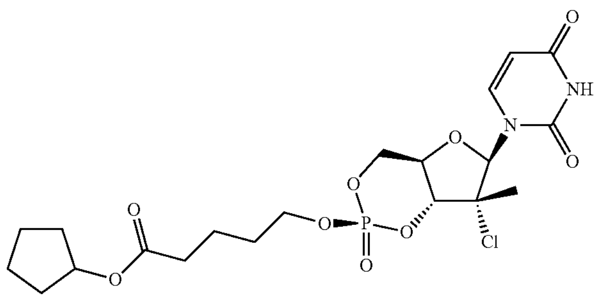 [SMILES: C[C@@]1(Cl)[C@@H]2O[P@@](=O)(OCCCCC(=O)OC3CCCC3)OC[C@H]2O[C@H]1n1ccc(=O)[nH]c1=O] | DMSO: 11.64 (1H, s), 7.77 (1H, d, J = 8.1 Hz), 6.43 (1H, s), 5.70 (1H, d, J = 8.1 Hz), 5.08-5.03 (1H, m), 4.73-4.63 (2H, m), 4.44 (1H, d, J = 9.4 Hz), 4.22 (1H, dd, J = 9.1, 14.7 Hz), 4.11 (2H, dd, J = 7.5, 16.3 Hz), 2.31 (2H, dd, J = 7.2, 7.2 Hz), 1.86-1.77 (2H, m), 1.73-1.53 (13H, m) | DMSO: −6.84 | S$_P$ | 507.0 | E | A |
| 19B | 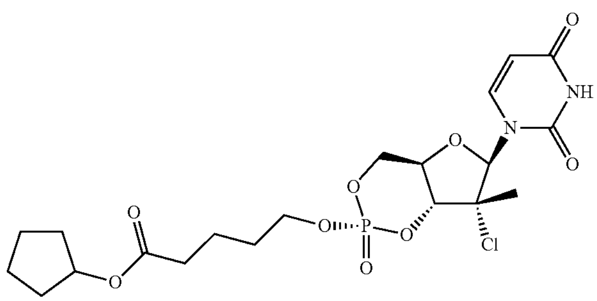 [SMILES: C[C@@]1(Cl)[C@@H]2O[P@](=O)(OCCCCC(=O)OC3CCCC3)OC[C@H]2O[C@H]1n1ccc(=O)[nH]c1=O] | DMSO: 11.62 (1H, s), 7.79 (1H, d, J = 8.1 Hz), 6.44 (1H, s), 5.67 (1H, d, J = 8.2 Hz), 5.09-5.04 (1H, m), 4.87 (1H, d, J = 9.5 Hz), 4.76-4.68 (2H, m), 4.41-4.33 (1H, m), 4.13-4.06 (2H, m), 2.29 (2H, dd, J = 7.1, 7.1 Hz), 1.84-1.76 (2H, m), 1.65-1.51 (12H, m) | DMSO: −5.73 | R$_P$ | 507.2 | E | A |
| 20A | 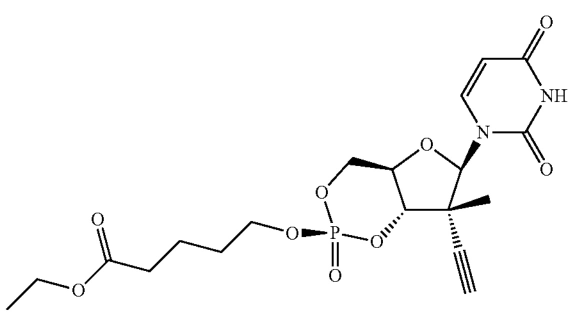 [SMILES: C#C[C@]1(C)[C@@H]2O[P@@](=O)(OCCCCC(=O)OCC)OC[C@H]2O[C@H]1n1ccc(=O)[nH]c1=O] | | DMSO: −6.65 | S$_P$ | 457.0 | F | A |
| 20B | 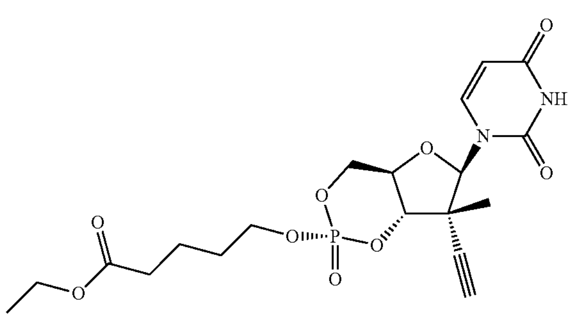 [SMILES: C#C[C@]1(C)[C@@H]2O[P@](=O)(OCCCCC(=O)OCC)OC[C@H]2O[C@H]1n1ccc(=O)[nH]c1=O] | | DMSO: −5.56 | R$_P$ | 457.0 | F | A |

TABLE 1-continued

| Cpd No. | STRUCTURE | NMR ¹H (ppm) | NMR $^{31}$P (ppm) | Stereo P | LC/MS (M + 1)⁺ | INT | METHOD |
|---|---|---|---|---|---|---|---|
| 21A or 21B | 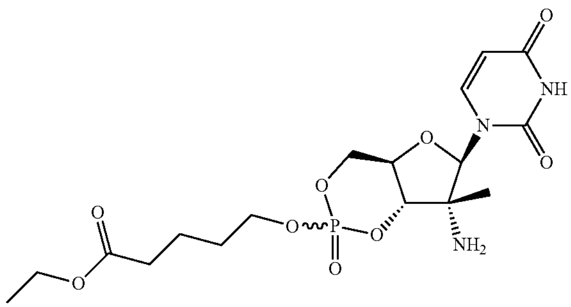 | | DMSO: −5.92 | $S_P$ or $R_P$ | 448.2 | F | A |
| 22A | 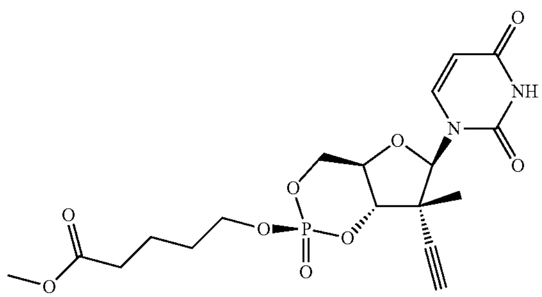 [SMILES: C#C[C@]1(C)[C@@H]2O[P@@](=O)(OCCCCC(=O)OC)OC[C@H]2O[C@H]1n1ccc(=O)[nH]c1=O] | | DMSO: −6.65 | $S_P$ | 443.2 | G | A |
| 22B | 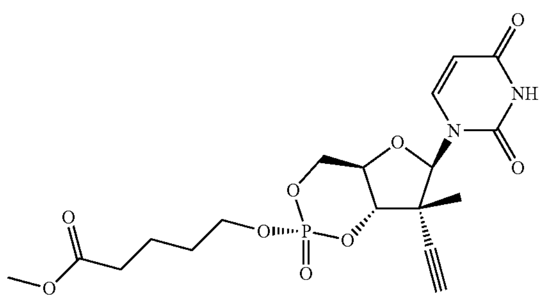 [SMILES: C#C[C@]1(C)[C@@H]2O[P@](=O)(OCCCCC(=O)OC)OC[C@H]2O[C@H]1n1ccc(=O)[nH]c1=O] | | DMSO: −5.56 | $R_P$ | 443.0 | G | A |
| 23A | 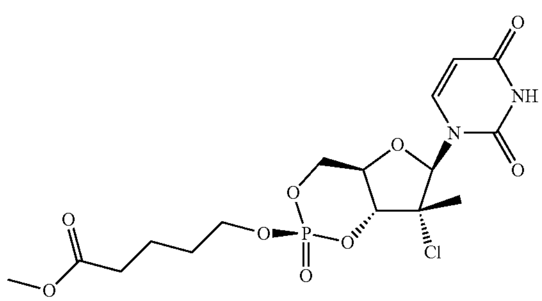 [SMILES: COC(=O)CCCCO[P@@]1(=O)OC[C@H]2O[C@@H](n3ccc(=O)[nH]c3=O)[C@](C)(Cl)[C@@H]2O1] | | DMSO: −6.84 | $S_P$ | 453.0 | G | A |
| 23B | 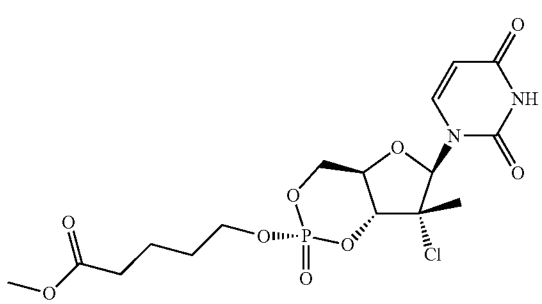 [SMILES: COC(=O)CCCCO[P@]1(=O)OC[C@H]2O[C@@H](n3ccc(=O)[nH]c3=O)[C@](C)(Cl)[C@@H]2O1] | | DMSO: −5.72 | $R_P$ | 453.0 | G | A |

TABLE 1-continued

| Cpd No. | STRUCTURE | NMR ¹H (ppm) | NMR ³¹P (ppm) | Stereo P | LC/MS (M + 1)⁺ | INT | METHOD |
|---|---|---|---|---|---|---|---|
| 24A | 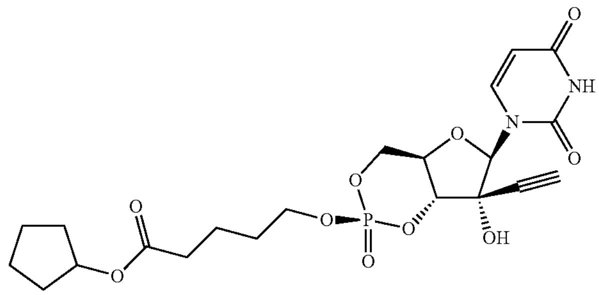 [SMILES: C#C[C@@]1(O)[C@@H]2O[P@@](=O)(OCCCCC(=O)OC3CCCC3)OC[C@H]2O[C@H]1n1ccc(=O)[nH]c1=O] | DMSO: 11.47 (1H, s), 7.78 (1H, d, J = 8.1 Hz), 7.18 (1H, s), 6.05 (1H, s), 5.67 (1H, d, J = 8.2 Hz), 5.09-5.04 (1H, m), 4.69-4.59 (2H, m), 4.37 (1H, d, J = 9.8 Hz), 4.17-4.06 (3H, m), 3.79 (1H, s), 2.31 (2H, dd, J = 7.1, 7.1 Hz), 1.86-1.77 (2H, m), 1.74-1.52 (10H, m) | DMSO: −6.36 | $S_P$ | 499.2 | E | B |
| 24B | 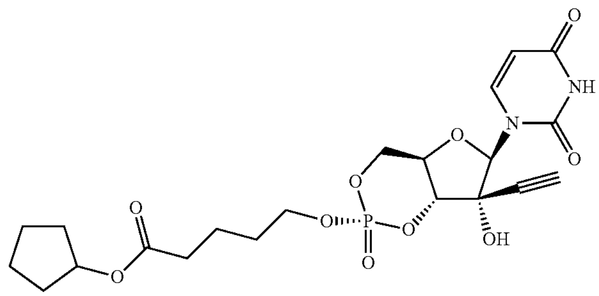 [SMILES: C#C[C@@]1(O)[C@@H]2O[P@](=O)(OCCCCC(=O)OC3CCCC3)OC[C@H]2O[C@H]1n1ccc(=O)[nH]c1=O] | DMSO: 11.47 (1H, s), 7.84 (1H, d, J = 8.2 Hz), 7.13 (1H, s), 6.06 (1H, s), 5.64 (1H, d, J = 8.1 Hz), 5.09-5.04 (1H, m), 4.77-4.61 (3H, m), 4.30-4.22 (1H, m), 4.10-4.04 (2H, m), 3.83 (1H, s), 2.29 (2H, dd, J = 7.2, 7.2 Hz), 1.86-1.78 (2H, m), 1.67-1.51 (10H, m) | DMSO: −5.21 | $R_P$ | 499.2 | E | B |
| 25A | 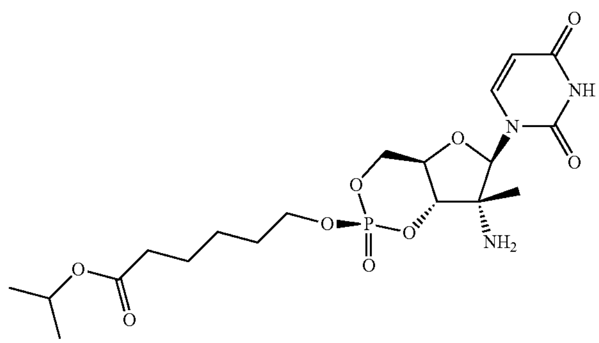 [SMILES: CC(C)OC(=O)CCCCCO[P@@]1(=O)OC[C@H]2O[C@@H](n3ccc(=O)[nH]c3=O)[C@](C)(N)[C@@H]2O1] | | DMSO: −5.92 | $S_P$ | 476.2 | H | A |
| 25B | 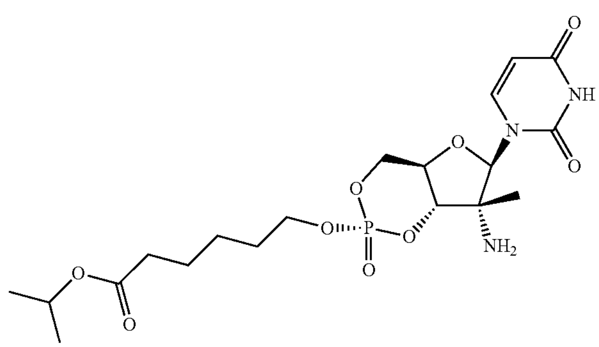 [SMILES: CC(C)OC(=O)CCCCCO[P@]1(=O)OC[C@H]2O[C@@H](n3ccc(=O)[nH]c3=O)[C@](C)(N)[C@@H]2O1] | | DMSO: −4.58 | $R_P$ | 476.2 | H | A |
| 26A | 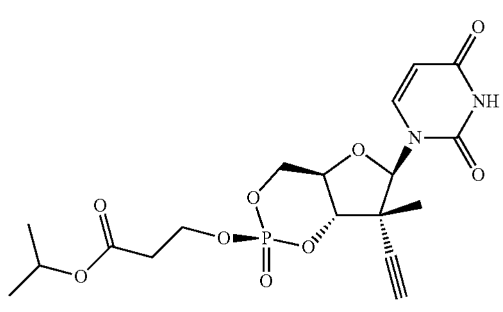 [SMILES: C#C[C@]1(C)[C@@H]2O[P@@](=O)(OCCC(=O)OC(C)C)OC[C@H]2O[C@H]1n1ccc(=O)[nH]c1=O] | | DMSO: −7.72 | $S_P$ | 443.2 | I | C |

TABLE 1-continued

| Cpd No. | STRUCTURE | NMR ¹H (ppm) | NMR ³¹P (ppm) | Stereo P | LC/MS (M + 1)⁺ | INT | METHOD |
|---|---|---|---|---|---|---|---|
| 26B | 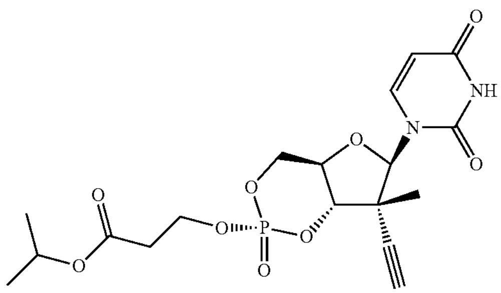 [SMILES: C#C[C@]1(C)[C@@H]2O[P@](=O)(OCCC(=O)OC(C)C)OC[C@H]2O[C@H]1n1ccc(=O)[nH]c1=O] | | DMSO: −4.65 | $R_P$ | 443.2 | I | C |
| 27A | 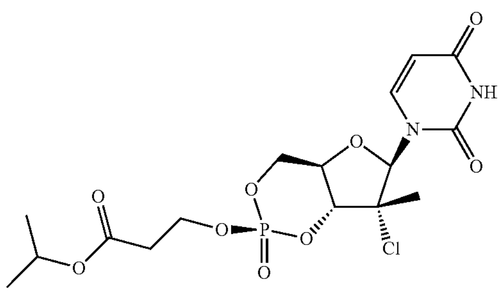 [SMILES: CC(C)OC(=O)CCO[P@@]1(=O)OC[C@H]2O[C@@H](n3ccc(=O)[nH]c3=O)[C@](C)(Cl)[C@@H]2O1] | | DMSO: −7.46 | $S_P$ | 453.0 | I | C |
| 27B | 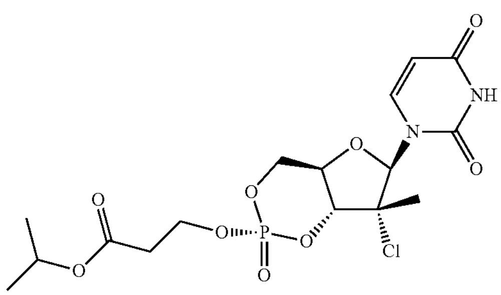 [SMILES: CC(C)OC(=O)CCO[P@]1(=O)OC[C@H]2O[C@@H](n3ccc(=O)[nH]c3=O)[C@](C)(Cl)[C@@H]2O1] | | DMSO: −6.14 | $R_P$ | 453.1 | I | C |
| 28A | 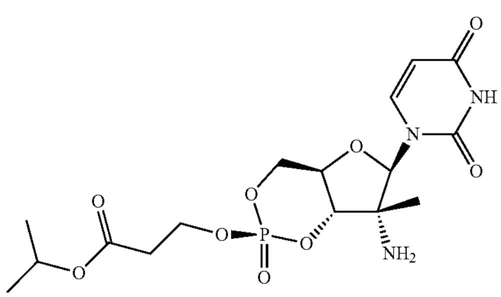 [SMILES: CC(C)OC(=O)CCO[P@@]1(=O)OC[C@H]2O[C@@H](n3ccc(=O)[nH]c3=O)[C@](C)(N)[C@@H]2O1] | DMSO: 11.52 (1H, s), 7.62 (1H, d, J = 8.2 Hz), 5.90 (1H, s), 5.64 (1H, d, J = 8.1 Hz), 4.99-4.89 (1H, m), 4.69-4.58 (1H, m), 4.50 (1H, dd, J = 9.7, 9.7 Hz), 4.29-4.13 (4H, m), 2.75 (2H, dd, J = 5.6, 5.6 Hz), 2.08-2.08 (2H, m), 1.21 (6H, dd, J = 5.9, 5.9 Hz), 1.04 (3H, s) | DMSO: −6.51 | $S_P$ | 434.0 | I | C |
| 28B | 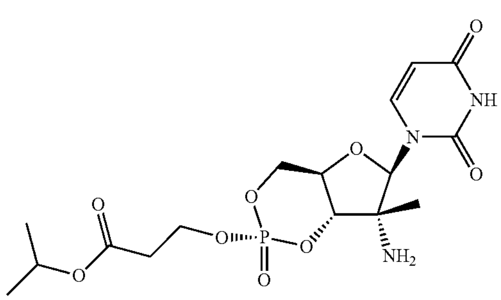 [SMILES: CC(C)OC(=O)CCO[P@]1(=O)OC[C@H]2O[C@@H](n3ccc(=O)[nH]c3=O)[C@](C)(N)[C@@H]2O1] | DMSO: 11.67 (1H, s), 8.63 (2H, s), 7.82 (1H, d, J = 8.1 Hz), 6.23 (1H, s), 5.72 (1H, dd, J = 1.3, 8.2 Hz), 4.98-4.90 (2H, m), 4.80-4.71 (1H, m), 4.67-4.58 (1H, m), 4.49-4.40 (1H, m), 4.36-4.25 (2H, m), 2.73 (2H, dd, J = 6.0, 6.0 Hz), 1.29-1.19 (9H, m) | DMSO: −5.78 | $R_P$ | 434.4 | I | C |

TABLE 1-continued

| Cpd No. | STRUCTURE | NMR ¹H (ppm) | NMR $^{31}$P (ppm) | Stereo P | LC/MS $(M + 1)^+$ | INT | METHOD |
|---|---|---|---|---|---|---|---|
| 29A or 29B | 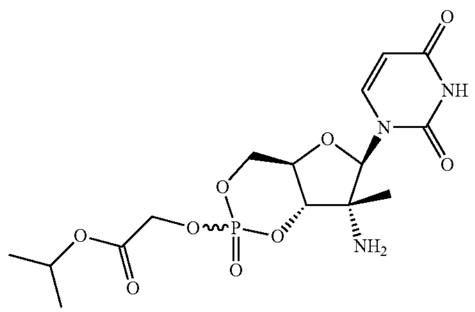 | | DMSO: −4.22 | $S_P$ or $R_P$ | 420.3 | J | A |

Example 9

Replicon Activity and Cytotoxicity Assays

To measure cell-based anti-HCV activity of the compounds of the present invention, replicon cells (1b-Con1) are seeded at 5000 cells/well in 96-well plates one day prior to treatment with a compound of the invention. Various concentrations of a test compound of the invention in DMSO are then added to the replicon cells, with the final concentration of DMSO at 0.5% and fetal bovine serum at 10% in the assay media. Cells are harvested three days post-dosing, and the replicon RNA level is determined using real-time RT-PCR (Taqman assay) with GAPDH RNA as endogenous control. $EC_{50}$ values are calculated from experiments with 10 serial twofold dilutions of the inhibitor in triplicate. To measure cytotoxicity in replicon cells of an inhibitor, an MTS assay is performed according to the manufacturer's protocol for CellTiter 96 Aqueous One Solution Cell Proliferation Assay (Promega, Cat #G3580) three days post dosing on cells treated identically as in replicon activity assays. $CC_{50}$ is the concentration of inhibitor that yields 50% inhibition compared to vehicle-treated cells. Cytotoxicity in other types of cells may be measured using the same MTS protocol.

Data were obtained using this method for selected compounds of the present invention, and are set forth below in Table 2. These data indicate that the compounds possess significant cytotoxicity windows over replicon activity.

Example 10

Determination of In Vivo Conversion of Prodrug to Nucleoside Triphosphate

The degree of conversion of a prodrug compound of the present invention to its corresponding nucleoside triphosphate (NTP) was measured in vivo using the procedure described below.

Liver samples were collected from either Wistar Hannover Rats or Beagle Dogs dosed with the prodrug via the freeze clamp procedure (animals anesthetized via isofluorane, the liver was clamped with modified clamps that are frozen in liquid nitrogen, then the clamped liver piece was placed in liquid nitrogen to ensure frozen completely; the liver clamp procedure was repeated to get a second piece of liver sample; samples stored at −80° C.). Liver samples were then homogenized using a a Spex Sample Prep Freezer/Mill (Cryomill); settings for the cryomill operation are 1 Cycle, 2 minute pre-chill time, 2 minute run time, 1 minute cool time, and a rate of 15 cycles/second (cps). Control liver samples collected from rats dosed with vehicle were cryomilled in the same manner. During this process it is imperative that anything that will come into contact with the liver samples remain frozen on dry ice at all times, such as all Cryomill sample containers/lids and spatulas.

The cryomilled control liver sample was used to generate the standard curve. An appropriate amount of cryomilled control liver sample was weighed out into a conical tube, depending on how many standard curves are needed, placed on wet ice and suspended with cold (approx. 0° C.) 70% Methanol/30% (20 mM EDTA/EGTA) that had been adjusted to pH 8 with sodium hydroxide at a ratio of 1:4 (liver:MeOH/EDTA-EGTA). The suspended liver homogenate was vortexed until a homogenous suspension was obtained. The standard curve ranged from 10 ng/mL to 50,000 ng/mL of NTP standard, as well as a QC sample at 10,000 ng/mL. A 500 μL aliquot of suspended control liver homogenate per each point on the standard curve and each QC was removed and placed into a 1.5 mL centrifuge tube, and 125 μL of each corresponding standard curve or QC standard solution was added to each individual control aliquot and re-vortexed. Liver sample aliquots were centrifuged at 4° C., 3645×g, for 10 minutes, and 450 μL of the supernatant was aliquoted into a 2 mL Square 96 well bioanalytical plate. Single and double blank samples are also generated from the suspended control liver homogenate using the procedure above, substituting the 125 μL of standard solution with 125 μL of water.

Approximately 1-2 grams of the cryomilled liver sample was weighed out into a 50 mL conical tube and placed on wet ice and suspended with cold 70% Methanol/30% (20 mM EDTA/EGTA) that had been adjusted to pH 8 with sodium hydroxide at a ratio of 1:4 (liver:MeOH/EDTA-EGTA); the remaining cryomilled liver sample was stored at −80° C. for possible re-assay if needed. The suspended liver homogenate was vortexed until a homogenous suspension was obtained. A 500 μL aliquot of each unknown liver sample was removed and placed into a 1.5 mL centrifuge tube, and 125 μL of water was added to each aliquot and re-vortexed. Standard curve/QC liver sample aliquots were centrifuged at 4° C., 3645×g, for 10 minutes, and 450 μL of the supernatant was aliquoted into a 2 mL square 96 well bioanalytical plate, and an appropriate internal standard was added to all sample wells, standard curve/QC wells, and the single blank well. The sample plate was stored at −80° C. until analysis and results were reported in μM of NTP measured.

Results are provided in Table 2 below.

TABLE 2

| Applic. Cpd # | EC50 (1b) Range [1] | CC50 (EDU) Range [2] | TP Mouse AUC0-24 1 mpk Range [3] |
|---|---|---|---|
| 2 | ND | ND | ND |
| 2A | ND | ND | ND |
| 2B | ND | ND | ND |
| 1A | ++ | ++ | + |
| 1B | +++ | ++ | + |
| 3B | ++ | ++ | + |
| 3A | + | ++ | + |
| 4A | + | ++ | ++ |
| 4B | ++ | ++ | ++ |
| 5A | + | ++ | +++ |
| 5B | + | ++ | ++ |
| 6B | ++++ | ++ | ND |
| 6A | + | ++ | ND |
| 7A or 7B | ++++ | ND | ND |
| 8A | ++ | ++ | ND |
| 8B | +++ | ++ | ND |
| 9A | + | ++ | + |
| 9B | ++++ | ++ | + |
| 10A | + | ++ | ND |
| 10B | + | ++ | ND |
| 11B | +++ | ++ | ++ |
| 11A | ++ | ++ | ++ |
| 12A | + | ++ | ++ |
| 12B | + | ++ | ++ |
| 13A | + | ++ | + |
| 13B | ++ | ++ | ++ |
| 14 | + | ++ | ND |
| 15A | + | ++ | + |
| 15B | + | ++ | +++ |
| 14A | + | ++ | + |
| 14B | + | ++ | ++ |
| 16B | ++ | ++ | +++ |
| 17B | ++ | ++ | +++ |
| 18B | ++ | ++ | +++ |
| 18A | ++ | ++ | + |
| 19B | +++ | ++ | ++ |
| 16A | + | ++ | + |
| 19A | ++ | ++ | + |
| 20B | + | ++ | +++ |
| 20A | + | ++ | + |
| 21A or 21B | + | ++ | ND |
| 22A | + | ++ | ND |
| 22B | + | ++ | ND |
| 23A | +++ | ++ | ND |
| 23B | ++ | ++ | ND |
| 17A | + | ++ | + |
| 24A | ++ | ++ | ND |
| 24A | ++ | ++ | ND |
| 24B | ++++ | ++ | ND |
| 24B | ++++ | ++ | ND |
| 25A | + | ND | ND |
| 25B | + | ND | ND |
| 26A | + | ++ | + |
| 26B | + | ++ | + |
| 27B | ++ | ND | ND |
| 27A | ++ | ND | ND |
| 28B | + | ++ | ND |
| 28A | + | ++ | ND |
| 29A or 29B | ND | ND | ++ |

[1] EC$_{50}$ is provided as follows:
++++ ≤ 250 nM, 250 nM < +++ ≤ 1 μM, 1 μM < ++ ≤ 10 μM, and + > 10 μM
[2] CC$_{50}$ is provided as follows:
+ ≤ 50 μM, ++ > 50 μM
[3] TP Mouse AUC0-24 1 mpk is provided as follows:
+ ≤ 50, 50 < ++ ≤ 150, and +++ > 150
ND = Not Determined Uses of the Cyclic Phosphate Substituted Nucleoside Compounds Treatment or Prevention of HCV Infection The Cyclic Phosphate Substituted Nucleoside Compounds are useful in the inhibition of HCV, the treatment of HCV infection and/or reduction of the likelihood or severity of symptoms of HCV infection and the inhibition of HCV viral replication and/or HCV viral production in a cell-based system. For example, the Cyclic Phosphate Substituted Nucleoside Compounds are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Cyclic Phosphate Substituted Nucleoside Compound or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Cyclic Phosphate Substituted Nucleoside Compounds are also useful in the preparation and execution of screening assays for antiviral compounds. For example the Cyclic Phosphate Substituted Nucleoside Compounds are useful for identifying resistant HCV replicon cell lines harboring mutations within NS5B, which are excellent screening tools for more powerful antiviral compounds. Furthermore, the Cyclic Phosphate Substituted Nucleoside Compounds are useful in establishing or determining the binding site of other antivirals to the HCV NS5B polymerase.

The compositions and combinations of the present invention may be useful for treating a patient suffering from infection related to any HCV genotype. HCV types and subtypes may differ in their antigenicity, level of viremia, severity of disease produced, and response to interferon therapy as described in Holland et al., *Pathology*, 30(2):192-195 (1998). The nomenclature set forth in Simmonds et al., *J Gen Virol*, 74(Pt11):2391-2399 (1993) is widely used and classifies isolates into six major genotypes, 1 through 6, with two or more related subtypes, e.g., 1a and 1b.

In one aspect, the present invention provides for the use of a compound of formula (I), or a pharmaceutically acceptable salt thereof, for inhibiting HCV NS5B activity or for preventing and/or treating infection by HCV in a patient in need thereof.

Combination Therapy

In another embodiment, the present methods for treating or preventing HCV infection can further comprise the administration of one or more additional therapeutic agents which are not Cyclic Phosphate Substituted Nucleoside Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Cyclic Phosphate Substituted Nucleoside Compound (which may include two or more different 2'-Substituted Nucleoside Derivatives), or a pharmaceutically acceptable salt thereof, and (ii) at least one additional therapeutic agent that is other than a Cyclic Phosphate Substituted Nucleoside Compound, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Cyclic Phosphate Substituted Nucleoside Compound and an additional therapeutic agent may be present in fixed amounts (dosage amounts) in a single dosage unit (e.g., a capsule, a tablet and the like).

In one embodiment, the at least one Cyclic Phosphate Substituted Nucleoside Compound is administered during a time when the additional therapeutic agent(s) exert their prophylactic or therapeutic effect, or vice versa.

In another embodiment, the at least one Cyclic Phosphate Substituted Nucleoside Compound and the additional therapeutic agent(s) are administered in doses commonly employed when such agents are used as monotherapy for treating a viral infection.

In another embodiment, the at least one Cyclic Phosphate Substituted Nucleoside Compound and the additional therapeutic agent(s) are administered in doses lower than the doses commonly employed when such agents are used as monotherapy for treating a viral infection.

In still another embodiment, the at least one Cyclic Phosphate Substituted Nucleoside Compound and the additional therapeutic agent(s) act synergistically and are administered in doses lower than the doses commonly employed when such agents are used as monotherapy for treating a viral infection.

In one embodiment, the at least one Cyclic Phosphate Substituted Nucleoside Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HCV infection.

The at least one Cyclic Phosphate Substituted Nucleoside Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Cyclic Phosphate Substituted Nucleoside Compound and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, one or more compounds of the invention are administered with one or more additional therapeutic agents, including but not limited to the therapeutic agents described, supra.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In another embodiment, one or more compounds of the present invention are administered with one additional therapeutic agent selected from an HCV protease inhibitor, an interferon, a pegylated interferon and ribavirin. In another embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin, or a pharmaceutically acceptable salt thereof.

In still another embodiment, one or more compounds of the present invention are administered with two additional therapeutic agents selected from an HCV protease inhibitor, an HCV replication inhibitor, a nucleoside, an interferon, a pegylated interferon and ribavirin, or a pharmaceutically acceptable salt thereof.

In another embodiment, one or more compounds of the present invention are administered with an HCV protease inhibitor and ribavirin. In another specific embodiment, one or more compounds of the present invention are administered with a pegylated interferon and ribavirin, or a pharmaceutically acceptable salt thereof.

In another embodiment, one or more compounds of the present invention are administered with three additional therapeutic agents selected from an HCV protease inhibitor, an HCV replication inhibitor, a nucleoside, an interferon, a pegylated interferon and ribavirin, or a pharmaceutically acceptable salt thereof.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir, or a pharmaceutically acceptable salt thereof.

In a further embodiment, one or more compounds of the present invention are administered with ribavirin, interferon and an HCV polymerase inhibitor.

In another embodiment, one or more compounds of the present invention are administered with pegylated-interferon alpha and ribavirin, or a pharmaceutically acceptable salt thereof.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In one embodiment, the additional therapeutic agents comprise an HCV protease inhibitor and an HCV NS5A inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), RG7128 (Roche/Pharmasset), Sofosbuvir (Gilead), PSI-938 (Pharmasset-Gilead), PSI-879 (Pharmasset-Gilead), PSI-661 (Pharmasset), PF-868554/filibuvir (Pfizer), VCH-759/VX-759 (ViroChem Pharma/Vertex), HCV-371 (Wyeth/ViroPharma), HCV-796 (Wyeth/ViroPharma), IDX-184 (Idenix), IDX-375 (Idenix), NM-283 (Idenix/Novartis), MK-3682 (Merck), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3682 (Merck), VCH-222/VX-222 (ViroChem/Vertex), VCH-916 (ViroChem), VCH-716 (ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development,* 7(4):446 (2004); Tan et al., *Nature Reviews,* 1:867 (2002); and Beaulieu et al., *Current Opinion in Investigational Drugs,* 5:838 (2004), as well as pharmaceutically acceptable salts of any of the above agents.

Other HCV polymerase inhibitors useful in the present compositions and methods include, but are not limited to, those disclosed in International Publication Nos. WO 08/082484, WO 08/082488, WO 08/083351, WO 08/136815, WO 09/032116, WO 09/032123, WO 09/032124 and WO 09/032125; and the following compounds:

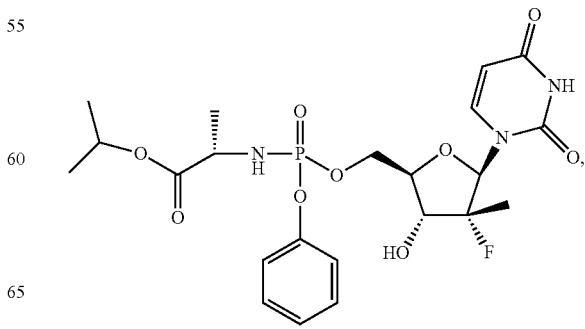

-continued

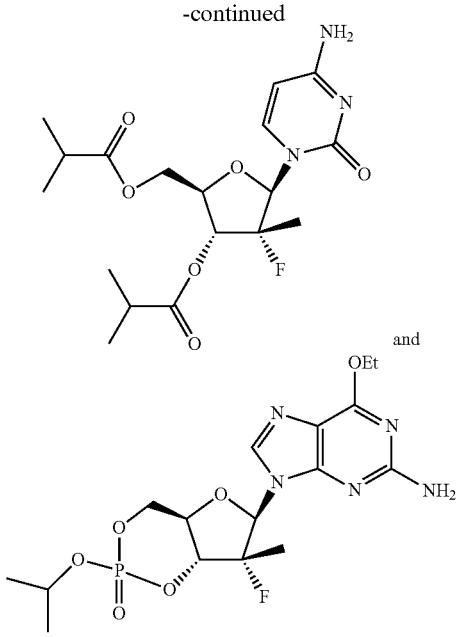

and pharmaceutically acceptable salts thereof.

Interferons useful in the present compositions and methods include, but are not limited to, interferon alfa-2a, interferon alfa-2b, interferon alfacon-1 and petroleum etherG-interferon alpha conjugates. "PEG-interferon alpha conjugates" are interferon alpha molecules covalently attached to a petroleum etherG molecule. Illustrative petroleum etherG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name petroleum etherG-Intron™ from Schering-Plough Corporation), interferon alpha-2b-XL (e.g., as sold under the trade name petroleum etherG-Intron™), interferon alpha-2c (Berofor Alpha™, Boehringer Ingelheim, Ingelheim, Germany), petroleum etherG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Examples of viral protease inhbitors useful in the present compositions and methods include, but are not limited to, an HCV protease inhibitor. Examples of HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), EA-058 (Abbott/Enanta), EA-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), grazoprevir (Merck), BMS-650032 (Bristol-Myers Squibb), VX-985 (Vertex) and PHX1766 (Phenomix), as well as pharmaceutically acceptable salts of any of the above agents.

Viral replication inhibitors useful in the present compositions and methods include, but are not limited to, HCV replicase inhibitors, IRES inhibitors, NS4A inhibitors, NS3 helicase inhibitors, NSSA inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine, as well as pharmaceutically acceptable salts of any of the above agents.

HCV NS5A inhibitors useful in the present compositions and methods include, but are not limited to, ACH-2928 (Achilon), A-832 (Arrow Therpeutics), AZD-7295 (Astra Zeneca/Arrow), GS-5885 (Gilead), Ledipasvir (Gilead), Velpatasvir (Gilead), Samatasvir (Merck), PPI-461 (Presidio), PPI-1301 (Presidio), BMS-824383 (Bristol-Myers Squibb), BMS-790052 (Bristol-Myers Squibb), elbasvir (Merck) and ruzasvir (Merck), as well as pharmaceutically acceptable salts of any of the above agents. Additional HCV NS5A inhibitors useful as second additional therapeutic agents in the present compositions and methods include, but are not limited to those disclosed in International Publication No. WO 2010/111483.

HCV replicase inhibitors useful in the present compositions and methods include, but are not limited to, those disclosed in U.S. Patent Publication No. US20090081636.

The doses and dosage regimen of the other agents used in the combination therapies of the present invention for the treatment or prevention of HCV infection may be determined using the attending clinician, taking into consideration the approved doses and dosage regimen in the package insert; the age, sex and general health of the patient; and the type and severity of the viral infection or related disease or disorder. When administered in combination, the Cyclic Phosphate Substituted Nucleoside Compound(s) and the other agent(s) may be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one Cyclic Phosphate Substituted Nucleoside Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

Due to their activity, the Cyclic Phosphate Substituted Nucleoside Compounds are useful in veterinary and human medicine. As described above, the Cyclic Phosphate Substituted Nucleoside Compounds are useful for treating or preventing HCV infection in a patient in need thereof.

When administered to a patient, the Cyclic Phosphate Substituted Nucleoside Compounds may be administered as a component of a composition that comprises a pharmaceutically acceptable carrier or vehicle. The present invention provides pharmaceutical compositions comprising an effective amount of at least one Cyclic Phosphate Substituted Nucleoside Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Cyclic Phosphate Substituted Nucleoside Compounds are administered orally.

In another embodiment, the one or more Cyclic Phosphate Substituted Nucleoside Compounds are administered intravenously.

In one embodiment, a pharmaceutical preparation comprising a Cyclic Phosphate Substituted Nucleoside Compound is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Cyclic Phosphate Substituted Nucleoside Compound(s) by weight or volume. In various embodiments, the present compositions can contain, in one embodiment, from about 1% to about 70% or from about 5% to about 60% of the Cyclic Phosphate Substituted Nucleoside Compound(s) by weight or volume.

The quantity of Cyclic Phosphate Substituted Nucleoside Compound in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Cyclic Phosphate Substituted Nucleoside Compounds will be regulated according to the judgment of the attending clinician considering such factors as age, condition and size of the patient as well as severity of the symptoms being treated. Generally, a total daily dosage of the Cyclic Phosphate Substituted Nucleoside Compounds range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Cyclic Phosphate Substituted Nucleoside Compound or a pharmaceutically acceptable salt thereof; (ii) one or more additional therapeutic agents that are not a Cyclic Phosphate Substituted Nucleoside Compound; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and wto additional therapeutic agents, each of which are independently selected from the group consisting of HCV antiviral agents, immunomodulators, and anti-infective agents.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:

1. A compound having the formula (I):

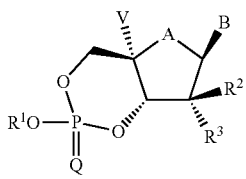

(I)

or a pharmaceutically acceptable salt thereof, wherein:
A is selected from O, S and $CH_2$;
B is:

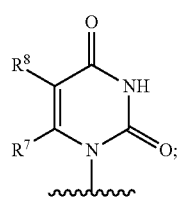

Q is O or S;
V is H, halo or $-N(R^{12})_2$;
$R^1$ is $-(CH_2)_m-C(O)OR^{13}$;
$R^2$ is selected from H, F, Cl, $C_1$-$C_3$ alkyl and $C_2$-$C_3$ alkynyl;
$R^3$ is selected from $C_1$-$C_6$ alkyl, $C_2$-$C_6$ alkenyl, $C_2$-$C_6$ alkynyl, $-OR^{12}$, F, Cl, $-N_3$, $-CN$ and $N(R^{12})_2$, such that if $R^2$ is F or $C_1$, then $R^3$ is other than F or Cl;
$R^4$, $R^5$, $R^7$ and $R^8$ are each independently selected from H, $C_1$-$C_6$ alkyl, $C_1$-$C_6$ haloalkyl, $C_1$-$C_6$ hydroxyalkyl, halo, $-OR^{14}$, $-SR^{14}$ and $-N(R^{14})_2$;
$R^6$, $R^9$, $R^{10}$ and $R^{11}$ are each independently selected from H, $C_1$-$C_6$ alkyl, $C_2$-$C_6$ alkenyl, $C_2$-$C_6$ alkynyl, $C_3$-$C_7$ cycloalkyl, 5- or 6-membered monocyclic heteroaryl, 9- or 10-membered bicyclic heteroaryl, halo, $-OR^{14}$, $-SR^{14}$, $-S(O)R^{14}$, $-S(O)_2R^{14}$, $-S(O)_2N(R^{14})_2$, $-NHC(O)OR^{14}$, $-NHC(O)N(R^{14})_2$, $C_1$-$C_6$ haloalkyl, $C_1$-$C_6$ hydroxyalkyl, $-O-(C_1$-$C_6$ haloalkyl), $-CN$, $-NO_2$, $-N(R^{14})_2$, $-NH(C_1$-$C_6$ alkylene)-(5- or 6-membered monocyclic heteroaryl), $-NH(C_1$-$C_6$ alkylene)-(9- or 10-membered bicyclic heteroaryl), $-C(O)R^{14}$, $-C(O)OR^{14}$, $-C(O)N(R^{14})_2$ and $-NHC(O)R^{14}$, wherein said $C_2$-$C_6$ alkenyl group and said $C_2$-$C_6$ alkynyl group may be optionally substituted with halo;
each occurrence of $R^{12}$ is independently selected from H, $C_1$-$C_6$ alkyl, $-C(O)R^{14}$ and $-C(O)OR^{14}$;
each occurrence of $R^{13}$ is independently selected from $C_1$-$C_6$ alkyl, $C_3$-$C_7$ cycloalkyl and $C_6$-$C_{10}$ aryl;
each occurrence of $R^{14}$ is independently selected from H, $C_1$-$C_6$ alkyl, $C_1$-$C_6$ haloalkyl, $C_1$-$C_6$ hydroxyalkyl, $-(C_1$-$C_3$ alkylene)$_n$-($C_3$-$C_7$ cycloalkyl), $-(C_1$-$C_3$ alkylene)$_n$-($C_6$-$C_{10}$ aryl), $-(C_1$-$C_3$ alkylene)$_n$-(4 to 7-membered heterocycloalkyl), $-(C_1$-$C_3$ alkylene)$_n$-(5- or 6-membered monocyclic heteroaryl) and $-(C_1$-$C_3$ alkylene)$_n$-(9- or 10-membered bicyclic heteroaryl);
m is 1, 2, 3, 4 or 5; and
each occurrence of n is independently 0 or 1.

2. The compound of claim 1, wherein A and Q are each O.

3. The compound of claim 1, wherein $R^2$ is methyl.

4. The compound of claim 1, wherein $R^3$ is selected from $-OH$, F, Cl, $-N_3$, $-CN$, $-C\equiv CH$ and $-NH_2$.

5. The compound of claim 1, having the formula (Ia):

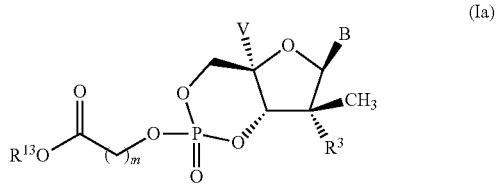

(Ia)

or a pharmaceutically acceptable salt thereof, wherein:
B is uracil;
$R^3$ is selected from $-OH$, F, $C_1$, $N_3$, $-CN$, $-C\equiv CH$ and $-NH_2$;
$R^{13}$ is $C_1$-$C_6$ alkyl or $C_3$-$C_7$ cycloalkyl; and
V is H or F; and
m is 1, 2, 3, 4 or 5.

6. The compound of claim 1, wherein m is 1.

7. The compound of claim 1, wherein m is 2.

8. The compound of claim 1, wherein m is 3.
9. The compound of claim 1, wherein m is 4.
10. The compound of claim 1, wherein m is 5.
11. The compound of claim 1, wherein $R^{13}$ is methyl, ethyl, isopropyl, n-butyl or cyclopentyl.
12. A compound having the structure:
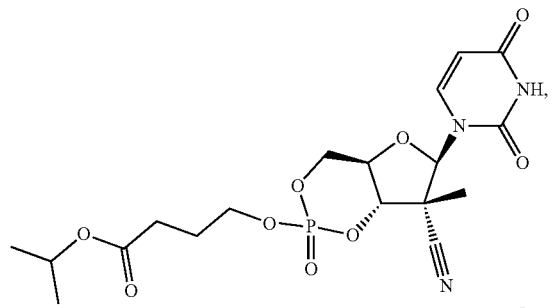
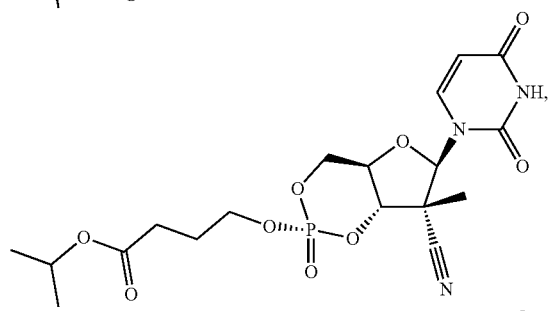
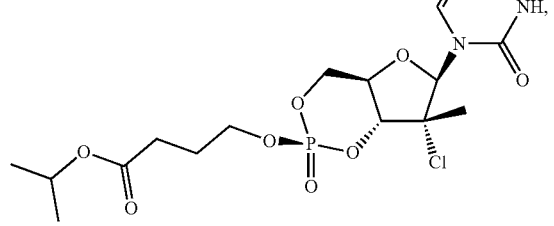
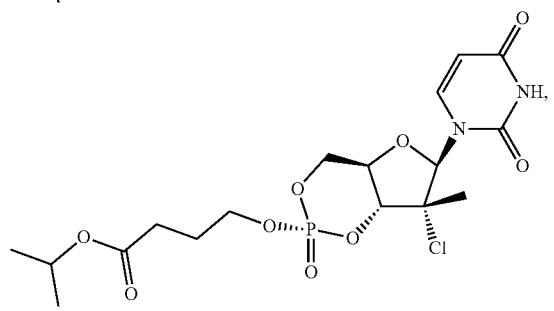
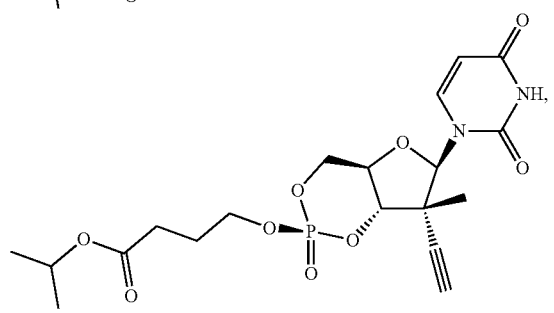
-continued
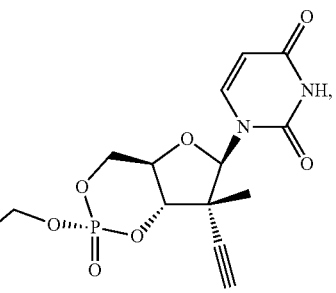
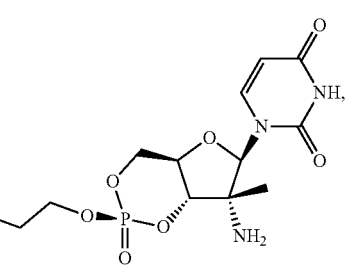
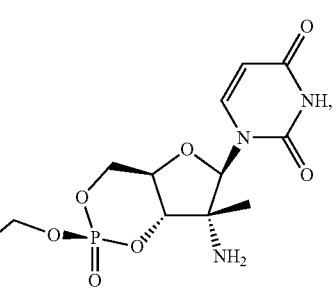
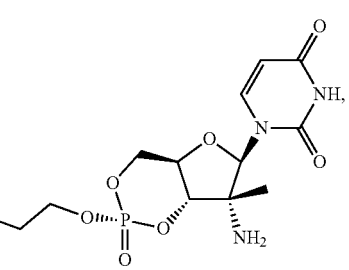
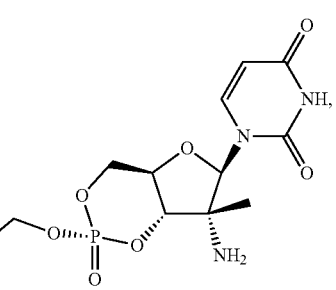

69
-continued
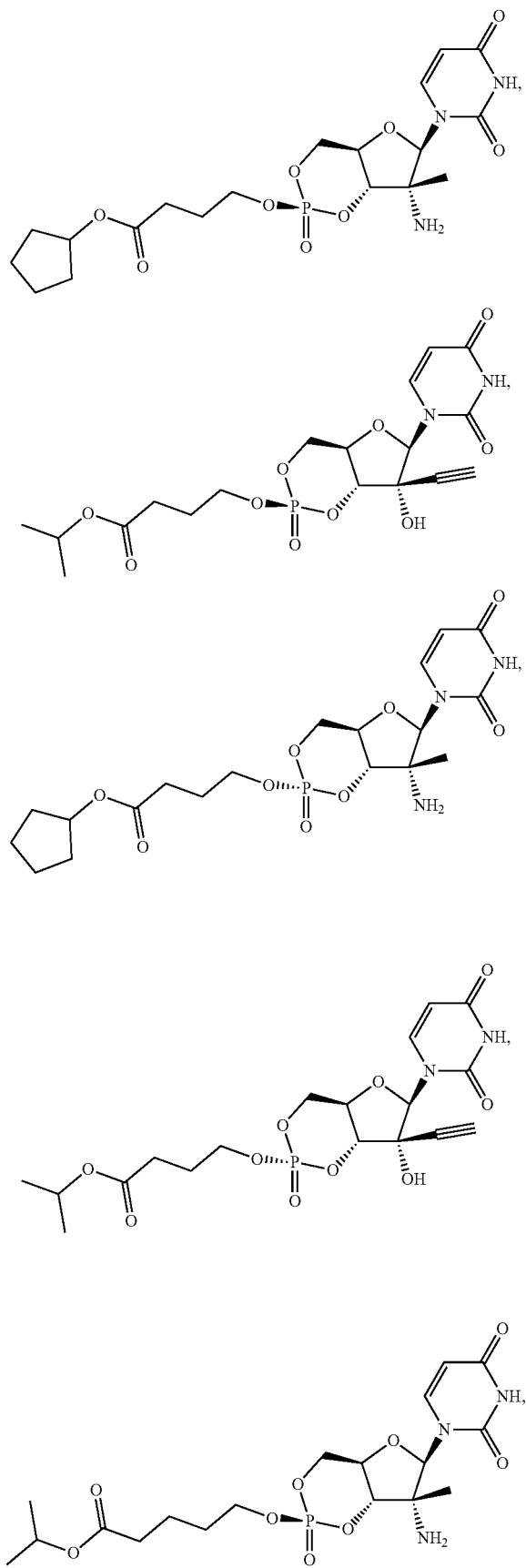
70
-continued
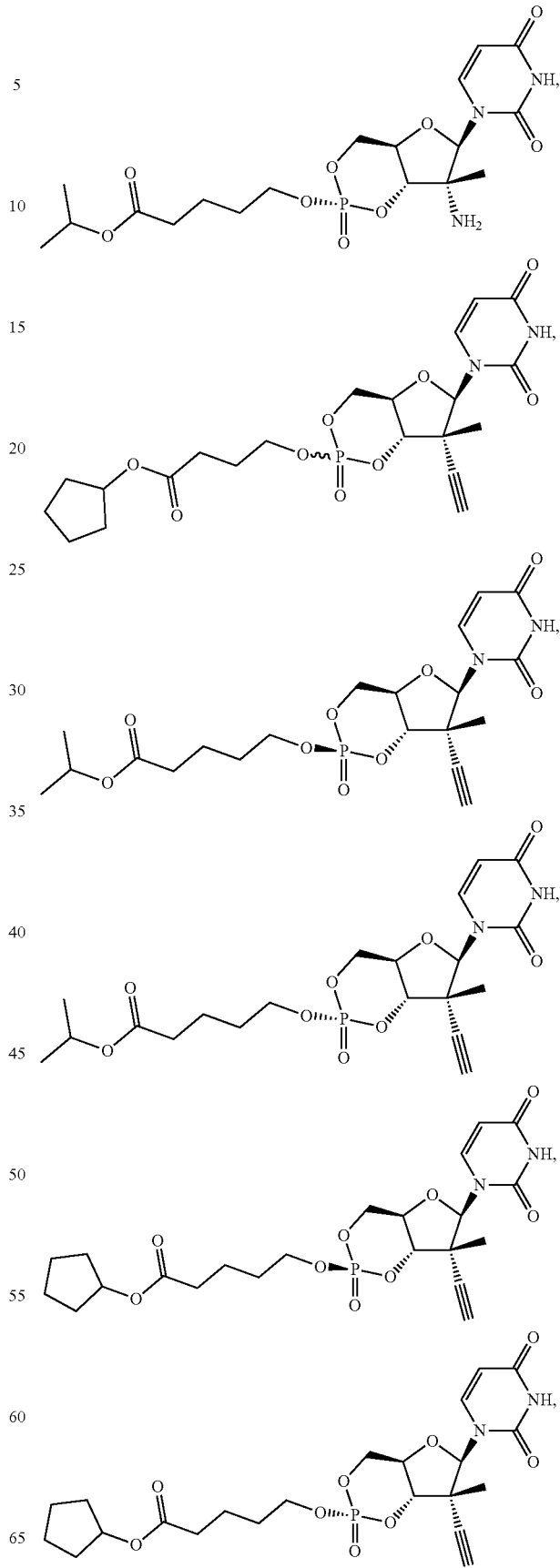

71
-continued
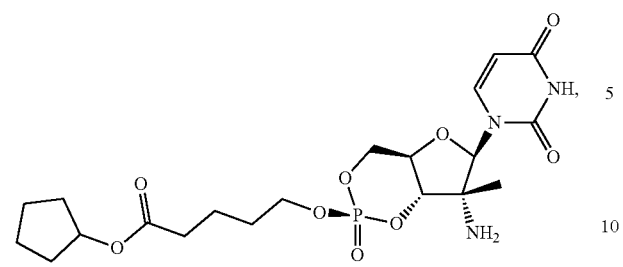
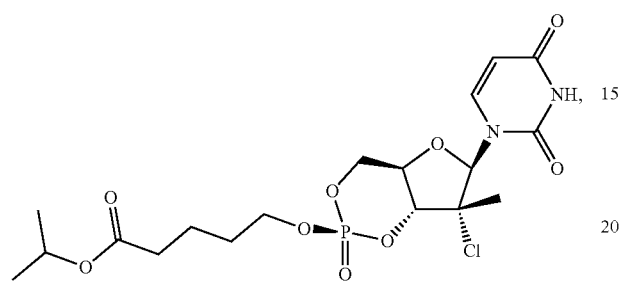
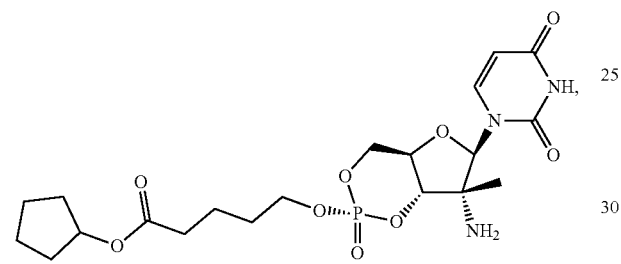
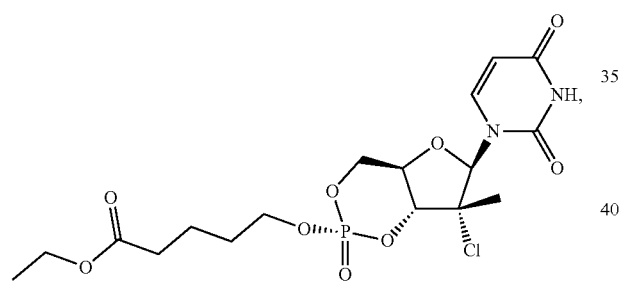
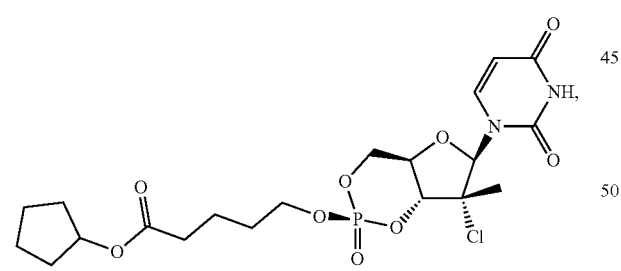
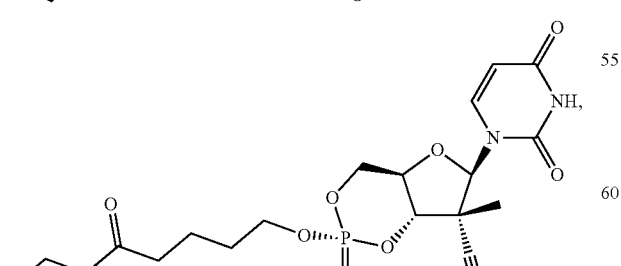
72
-continued
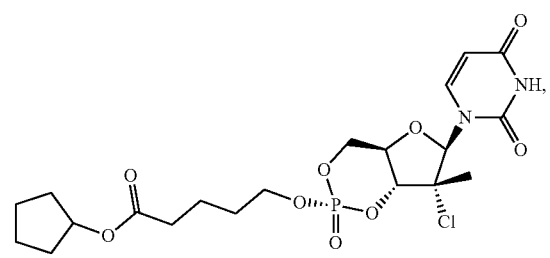
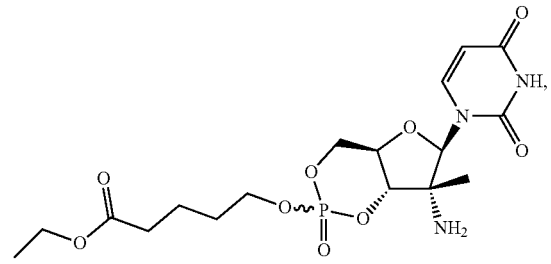
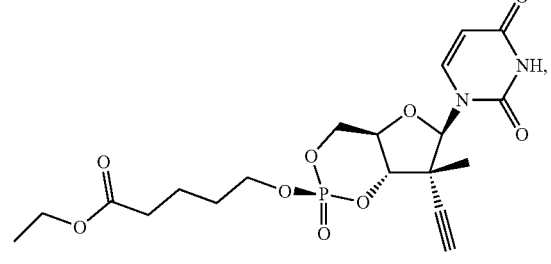
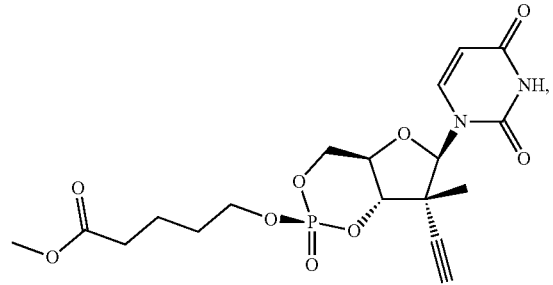
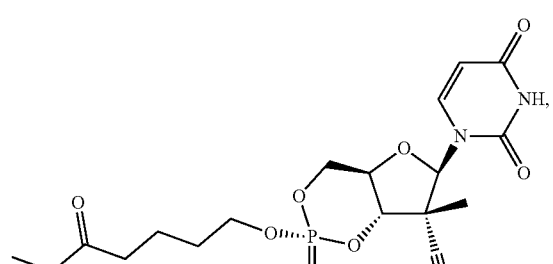
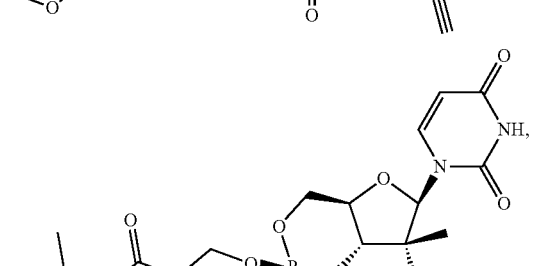

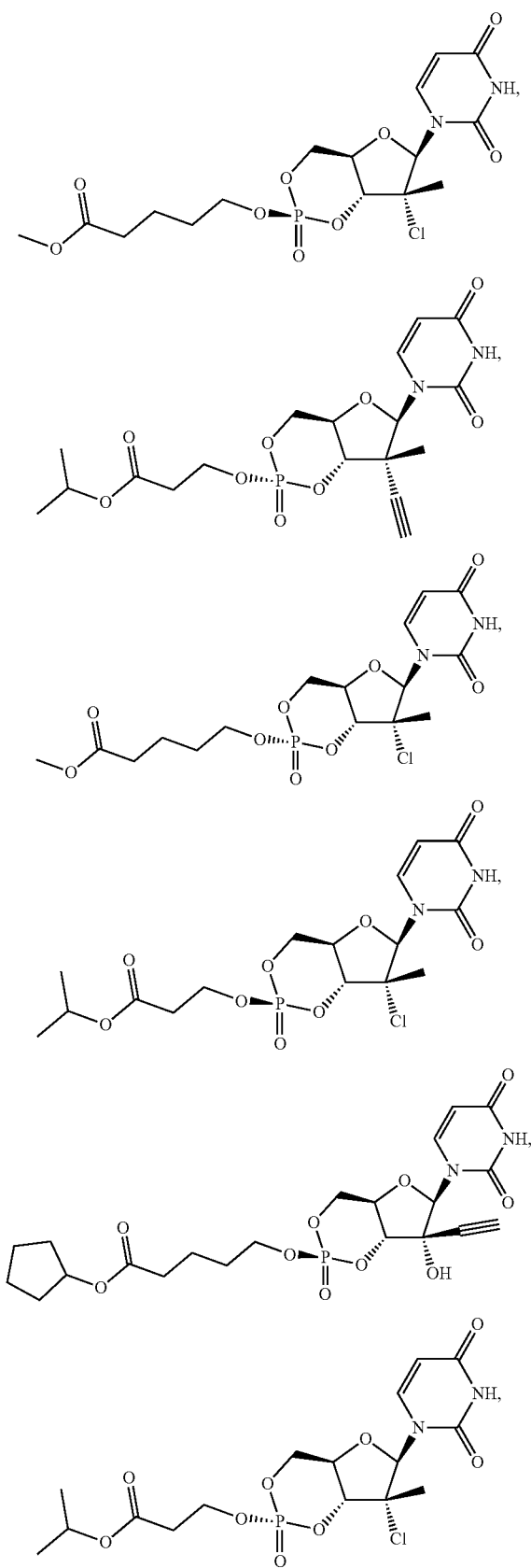
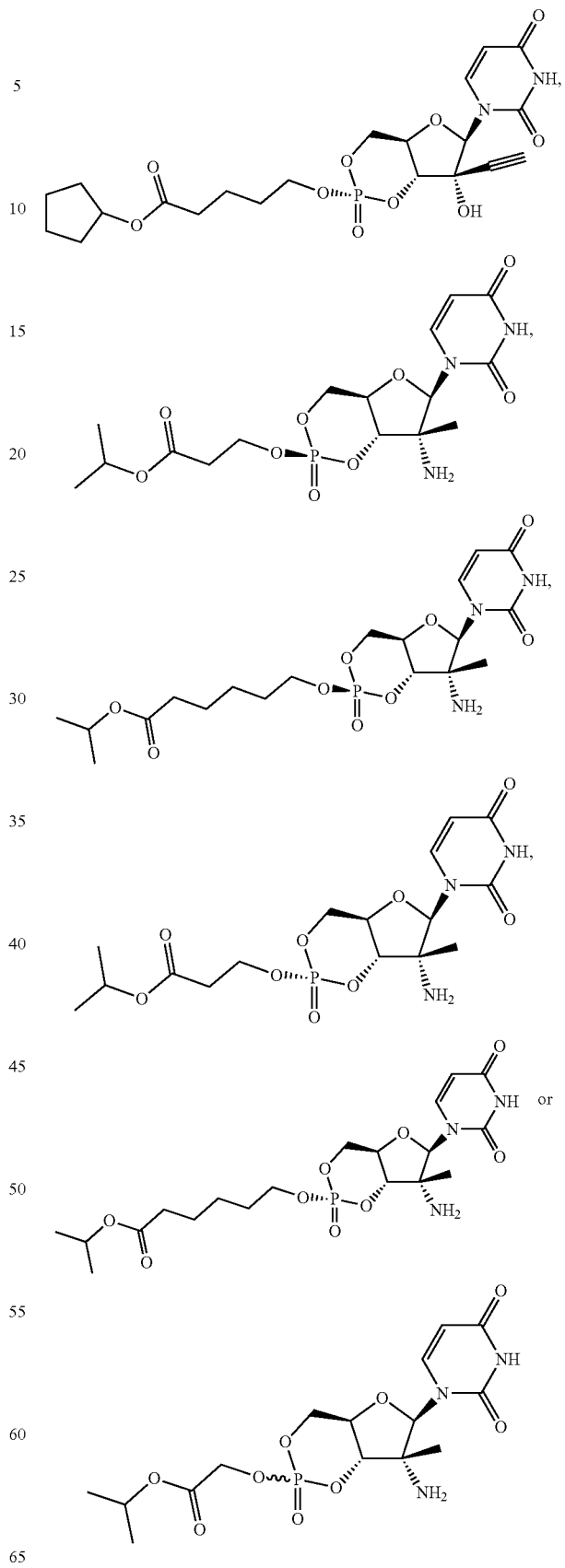
or a pharmaceutically acceptable salt thereof.

13. A pharmaceutical composition comprising an effective amount of the compound of claim 1, or a pharmaceutically acceptable salt thereof, and a pharmaceutically acceptable carrier.

14. The pharmaceutical composition of claim 13, further comprising a second therapeutic agent selected from the group consisting of HCV antiviral agents, immunomodulators, and anti-infective agents.

15. The pharmaceutical composition of claim 14, further comprising a third therapeutic agent selected from the group consisting of HCV protease inhibitors, HCV NS5A inhibitors and HCV NS5B polymerase inhibitors.

16. A method of treating a patient infected with HCV comprising the step of administering an amount of the compound of claim 1, or a pharmaceutically acceptable salt thereof, effective to treat infection by HCV in said patient.

17. The method of claim 16, further comprising the step of administering to said patient a second therapeutic agent selected from the group consisting of HCV antiviral agents, immunomodulators, and anti-infective agents.

\* \* \* \* \*